United States Patent
Weinfeld et al.

(10) Patent No.: US 10,087,448 B2
(45) Date of Patent: *Oct. 2, 2018

(54) SYNTHETIC LETHALITY IN CANCER

(71) Applicants: The Governors of the University of Alberta, Edmonton (CA); Alberta Health Services, Edmonton (CA)

(72) Inventors: Michael Weinfeld, Edmonton (CA); Todd Randall Mereniuk, Albert (CA); Edan Foley, Edmonton (CA); Dennis G. Hall, Edmonton (CA)

(73) Assignees: THE GOVERNORS OF THE UNIVERSITY OF ALBERTA, Edmonton (CA); ALBERTA HEALTH SERVICES, Edmonton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/788,254

(22) Filed: Jun. 30, 2015

(65) Prior Publication Data

US 2016/0083732 A1 Mar. 24, 2016

Related U.S. Application Data

(63) Continuation of application No. 13/883,569, filed as application No. PCT/CA2011/001229 on Nov. 7, 2011, now Pat. No. 9,115,406.

(60) Provisional application No. 61/410,666, filed on Nov. 5, 2010.

(51) Int. Cl.
| | | |
|---|---|---|
| *C12N 15/113* | (2010.01) |
| *A61P 35/00* | (2006.01) |
| *G01N 33/574* | (2006.01) |
| *A61K 31/00* | (2006.01) |
| *A61K 31/19* | (2006.01) |
| *A61K 31/366* | (2006.01) |
| *A61K 31/4015* | (2006.01) |
| *A61K 31/437* | (2006.01) |
| *A61K 31/4418* | (2006.01) |
| *A61K 31/4745* | (2006.01) |
| *A61K 31/52* | (2006.01) |
| *A61K 31/522* | (2006.01) |
| *A61K 31/555* | (2006.01) |
| *A61K 31/655* | (2006.01) |
| *A61K 31/7034* | (2006.01) |
| *A61K 31/7048* | (2006.01) |
| *A61K 31/7105* | (2006.01) |
| *A61K 31/713* | (2006.01) |
| *A61K 33/24* | (2006.01) |
| *C07D 471/04* | (2006.01) |
| *C12N 15/115* | (2010.01) |
| *C12Q 1/6886* | (2018.01) |
| *A61K 31/7088* | (2006.01) |
| *A61K 45/06* | (2006.01) |

(52) U.S. Cl.
CPC .......... *C12N 15/1137* (2013.01); *A61K 31/00* (2013.01); *A61K 31/19* (2013.01); *A61K 31/366* (2013.01); *A61K 31/4015* (2013.01); *A61K 31/437* (2013.01); *A61K 31/4418* (2013.01); *A61K 31/4745* (2013.01); *A61K 31/52* (2013.01); *A61K 31/522* (2013.01); *A61K 31/555* (2013.01); *A61K 31/655* (2013.01); *A61K 31/7034* (2013.01); *A61K 31/7048* (2013.01); *A61K 31/7088* (2013.01); *A61K 31/713* (2013.01); *A61K 31/7105* (2013.01); *A61K 33/24* (2013.01); *A61K 45/06* (2013.01); *C07D 471/04* (2013.01); *C12N 15/113* (2013.01); *C12N 15/115* (2013.01); *C12Q 1/6886* (2013.01); *G01N 33/57484* (2013.01); *C12N 2310/14* (2013.01); *C12N 2310/16* (2013.01); *C12N 2310/531* (2013.01); *G01N 2333/91215* (2013.01); *G01N 2800/52* (2013.01)

(58) Field of Classification Search
CPC ...... A61K 31/00; A61K 31/713; A61K 45/06; C12N 15/113; C12N 2310/14; C12Q 1/6886
USPC ........... 435/6.1, 6.11, 6.12, 91.1, 91.31, 455, 435/375, 458; 514/1, 2, 44; 536/23.1, 536/24.5; 424/9, 9.1
See application file for complete search history.

(56) References Cited

U.S. PATENT DOCUMENTS 9,115,406 B2 * 8/2015 Weinfeld ............... A61K 31/00

OTHER PUBLICATIONS

O'Brien et al, EMBO Mol. Med. vol. 1, pp. 297-299 (2009).*
Iglehart et al, New Eng. J. Med., vol. 361, No. 2, pp. 189-191 (2009).*
Emory Winship Cancer Institute, CancerQuest: Cancer Genes, pp. 1-48 (2016).*
Mereniuk et al., "Synthetic Lethal Targeting of PTEN-Deficient Cancer Cells Using Selective Disruption of Polynucleotide Kinase/Phosphatase", Mol Cancer Ther. Oct. 2013;12(10):2135-44. doi: 10.1158/1535-7163.MCT-12-1093. Epub Jul. 24, 2013.
Written Opinion for Application No. PCT/CA2011/001229, dated Feb. 13, 2012, 6 pages.

* cited by examiner

Primary Examiner — Jane J Zara
(74) Attorney, Agent, or Firm — Acuity Law Group, PC; Michael A. Whittaker

(57) ABSTRACT

There is described herein compounds, compositions and methods for inducing synthetic lethality in a cancer cell(s).

9 Claims, 39 Drawing Sheets

Specification includes a Sequence Listing.

Fig. 14A

PTEN:

| | |
|---|---|
| * Sequence 1) AAGGCGTATACAGGAACAATA | (SEQ ID NO: 2) |
| Sequence 2) ATCGATAGCATTTGCAGTATA | (SEQ ID NO: 3) |
| Sequence 3) TCGACTTAGACTTGACCTATA | (SEQ ID NO: 4) |
| Sequence 4) CAGATTGAATAGGACCTACTA | (SEQ ID NO: 5) | sequences with an "*" were used for verification

Fig. 14B

ING3:

| | |
|---|---|
| Sequence 1) CAGAATGCAATGGATCAACTA | (SEQ ID NO: 6) |
| Sequence 2) CACGGAAATGCGCGAGATGGA | (SEQ ID NO: 8) |
| * Sequence 3) AAGAGTCAGTGAATTCTTTAT | (SEQ ID NO: 9) |
| Sequence 4) CTGAGTGGAGGGAAGAGCAAA | (SEQ ID NO: 9) | sequences with an "*" were used for verification

Fig. 14C

PTPN6:

| | |
|---|---|
| Sequence 1) TAGGCCCTGATGAGAACGCTA | (SEQ ID NO:10) |
| * Sequence 2) CCGGAACAAATGCGTCCCATA | (SEQ ID NO: 11) |
| Sequence 3) CCAGTTCATTGAAACCACTAA | (SEQ ID NO: 12) |
| Sequence 4) CTGGACGTTTCTTGTGCGTGA | (SEQ ID NO: 13) | sequences with an "*" were used for verification

Fig. 14D

CDKN3:

Sequence 1) CACAATCAAGATCTGTATCAA (SEQ ID NO: 4)

* Sequence 2) TCGGGACAAATTAGCTGCACA (SEQ ID NO: 15)

Sequence 3) CTAAAGAGCTGTGGTATACAA (SEQ ID NO: 16)

Sequence 4) CACCAGTGTTATCAACTTGAA (SEQ ID NO: 17)

sequences with an "*" were used for verification

Fig. 14E

SMG1:

Sequence 1) CACCATGGTATTACAGGTTCA (SEQ ID NO: 18)

Sequence 2) ATCGATGTTGCCAGACTACTA (SEQ ID NO: 19)

Sequence 3) ACCATATCGCTTAGTAGTGAA (SEQ ID NO: 20)

Sequence 4) TGCGGCGTTATTTGAACTAAT (SEQ ID NO: 21)

* Verification sequence: GGAATTAGGTCTAACAGCA (Ambion) (SEQ ID NO: 22)

sequences with an "*" were used for verification

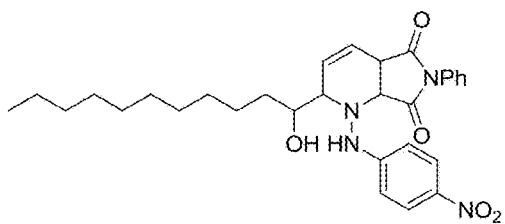

A12B4C3
2-(1-hydroxyundecyl)-1-((4-nitrophenyl)amino)-6-phenyl-6,7a-dihydro-1H-pyrrolo[3,4-b]pyridine-5,7(2H,4aH)-dione

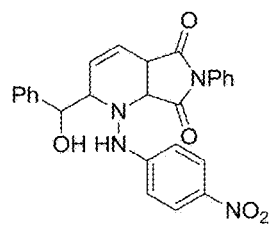

A1B4C3
2-(hydroxy(phenyl)methyl)-1-((4-nitrophenyl)amino)-6-phenyl-6,7a-dihydro-1H-pyrrolo[3,4-b]pyridine-5,7(2H,4aH)-dione

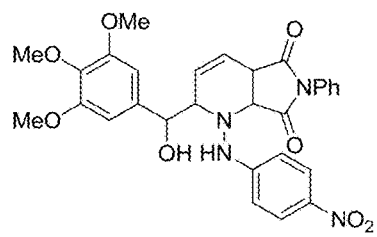

A6B4C3
2-(hydroxy(3,4,5-trimethoxyphenyl)methyl)-1-((4-nitrophenyl)amino)-6-phenyl-6,7a-dihydro-1H-pyrrolo[3,4-b]pyridine-5,7(2H,4aH)-dione

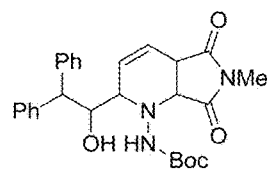

A26B11C2
tert-butyl(2-(1-hydroxy-2,2-diphenylethyl)-6-methyl-5,7-dioxo-2,4a,5,6,7,7a-hexahydro-1H-pyrrolo[3,4-b]pyridin-1-yl)carbamate

A39B1C2
2-(hydroxy(thiophen-2-yl)methyl)-6-methyl-1-(phenylamino)-6,7a-dihydro-1H-pyrrolo[3,4-b]pyridine-5,7(2H,4aH)-dione

Figure 15

Time (min)

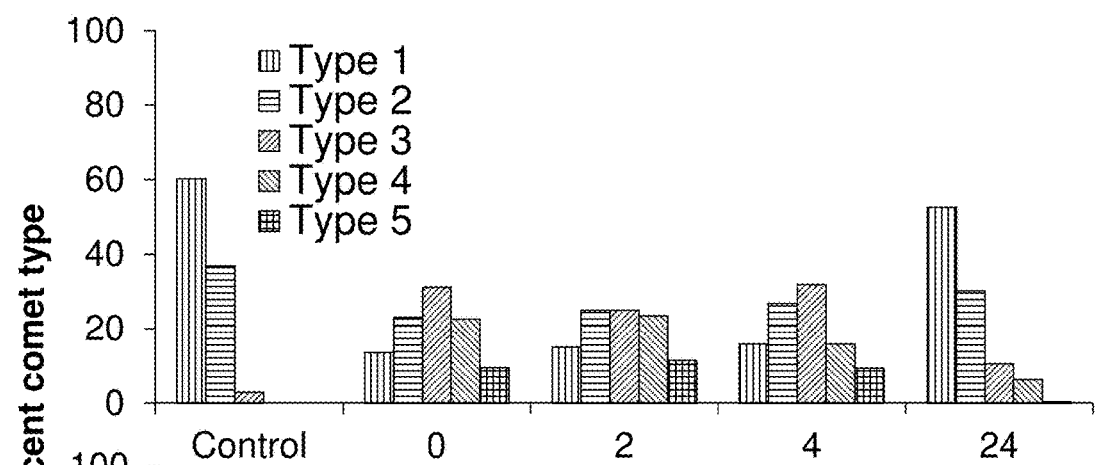
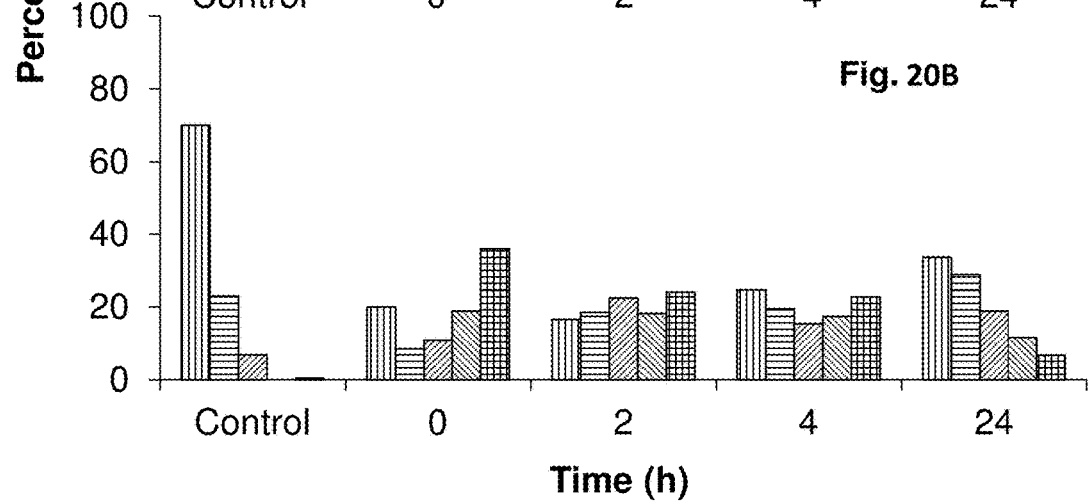
Fig. 20A
Fig. 20B

SEQUENCE LISTING

```
<160> NUMBER OF SEQ ID NOS: 22

<210> SEQ ID NO 1
<211> LENGTH: 19
<212> TYPE: DNA
<213> ORGANISM: Homo sapiens

<400> SEQUENCE: 1
agagatgacg gactcctct                                                 19

<210> SEQ ID NO 2
<211> LENGTH: 21
<212> TYPE: DNA
<213> ORGANISM: Homo sapiens

<400> SEQUENCE: 2
aaggcgtata caggaacaat a                                              21

<210> SEQ ID NO 3
<211> LENGTH: 21
<212> TYPE: DNA
<213> ORGANISM: Homo sapiens

<400> SEQUENCE: 3
```
atcgatagca tttgcagtat a                                              21

<210> SEQ ID NO 4
<211> LENGTH: 21
<212> TYPE: DNA
<213> ORGANISM: Homo sapiens

<400> SEQUENCE: 4
tcgacttaga cttgacctat a                                              21

<210> SEQ ID NO 5
<211> LENGTH: 21
<212> TYPE: DNA
<213> ORGANISM: Homo sapiens

<400> SEQUENCE: 5
cagattgaat aggacctact a                                              21

<210> SEQ ID NO 6
<211> LENGTH: 21
<212> TYPE: DNA
<213> ORGANISM: Homo sapiens

<400> SEQUENCE: 6
cagaatgcaa tggatcaact a                                              21

<210> SEQ ID NO 7
<211> LENGTH: 21
<212> TYPE: DNA
<213> ORGANISM: Homo sapiens

<400> SEQUENCE: 7
cacggaaatg cgcgagatgg a                                              21

<210> SEQ ID NO 8
<211> LENGTH: 21
<212> TYPE: DNA
<213> ORGANISM: Homo sapiens

<400> SEQUENCE: 8
aagagtcagt gaattcttta t                                              21

<210> SEQ ID NO 9
<211> LENGTH: 21
<212> TYPE: DNA
<213> ORGANISM: Homo sapiens

<400> SEQUENCE: 9
ctgagtggag ggaagagcaa a                                              21

<210> SEQ ID NO 10
<211> LENGTH: 21
<212> TYPE: DNA
<213> ORGANISM: Homo sapiens

<400> SEQUENCE: 10
taggccctga tgagaacgct a                                              21

<210> SEQ ID NO 11
<211> LENGTH: 21
<212> TYPE: DNA
<213> ORGANISM: Homo sapiens

<400> SEQUENCE: 11
ccggaacaaa tgcgtcccat a                                              21

<210> SEQ ID NO 12
<211> LENGTH: 21
<212> TYPE: DNA
<213> ORGANISM: Homo sapiens

<400> SEQUENCE: 12
ccagttcatt gaaaccacta a                                              21

<210> SEQ ID NO 13
<211> LENGTH: 21
<212> TYPE: DNA
<213> ORGANISM: Homo sapiens

<400> SEQUENCE: 13
ctggacgttt cttgtgcgtg a                                              21

<210> SEQ ID NO 14
<211> LENGTH: 21
<212> TYPE: DNA
<213> ORGANISM: Homo sapiens

<400> SEQUENCE: 14
cacaatcaag atctgtatca a                                              21

<210> SEQ ID NO 15
<211> LENGTH: 21
<212> TYPE: DNA
<213> ORGANISM: Homo sapiens

<400> SEQUENCE: 15
tcgggacaaa ttagctgcac a                                              21

<210> SEQ ID NO 16
<211> LENGTH: 21
<212> TYPE: DNA
<213> ORGANISM: Homo sapiens

<400> SEQUENCE: 16
ctaaagagct gtggtataca a                                              21

<210> SEQ ID NO 17
<211> LENGTH: 21
<212> TYPE: DNA
<213> ORGANISM: Homo sapiens

<400> SEQUENCE: 17
caccagtgtt atcaacttga a                                              21

<210> SEQ ID NO 18
<211> LENGTH: 21
<212> TYPE: DNA
<213> ORGANISM: Homo sapiens

<400> SEQUENCE: 18
caccatggta ttacaggttc a                                              21

<210> SEQ ID NO 19
<211> LENGTH: 21
<212> TYPE: DNA
<213> ORGANISM: Homo sapiens

```
<400> SEQUENCE: 19
atcgatgttg ccagactact a                                             21

<210> SEQ ID NO 20
<211> LENGTH: 21
<212> TYPE: DNA
<213> ORGANISM: Homo sapiens

<400> SEQUENCE: 20
accatatcgc ttagtagtga a                                             21

<210> SEQ ID NO 21
<211> LENGTH: 21
<212> TYPE: DNA
<213> ORGANISM: Homo sapiens

<400> SEQUENCE: 21
tgcggcgtta tttgaactaa t                                             21

<210> SEQ ID NO 22
<211> LENGTH: 19
<212> TYPE: DNA
<213> ORGANISM: Homo sapiens

<400> SEQUENCE: 22
ggaattaggt ctaacagca                                                19
```

SYNTHETIC LETHALITY IN CANCER

RELATED APPLICATIONS

The present invention is a continuation of U.S. patent application Ser. No. 13/883,569, which is the U.S. national phase patent application of International Application No. PCT/CA2011/001229, filed Nov. 7, 2011, which designated the U.S. and claims priority to U.S. Application No. 61/410,666 filed on Nov. 5, 2010, the contents of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jun. 30, 2015, is named BLG002CT_SeqListing.txt and is 4 kilobytes in size.

FIELD OF THE INVENTION

The field of the invention generally relates to compounds, compositions and methods for inducing synthetic lethality in cancer cells.

BACKGROUND OF THE INVENTION

Synthetic lethality occurs when a combination of two protein knockouts is lethal, however the corresponding single mutations are viable. The original concept of synthetic lethality as it relates to DNA repair was discovered in 2005. The Ashworth and Helleday groups published two papers back to back in Nature, outlining synthetic lethality between BRCA−/− cells and inhibition of poly(ADP-ribose) polymerase (PARP).

A major enzyme responsible for the phosphorylation of 5'-hydroxyl termini and dephosphorylation of 3'-phosphate termini in human cells is polynucleotide kinase/phosphatase (hPNKP) (13, 14). In the single-strand break (SSB) repair pathway hPNKP acts in concert with XRCC1, DNA polymerase β and DNA ligase III (15-17). PNKP-mediated DNA end-processing at double-strand breaks is a component of the nonhomologous end-joining (NHEJ) pathway and is dependent on DNA-PKcs and XRCC4 (18-20). In addition to its role in the repair of strand breaks produced directly by genotoxic agents, hPNKP has been implicated in the repair of strand breaks produced by enzymatic processes, including strand breaks introduced by the βδ-AP lyase activity of DNA glycosylases such as NEIL1 and NEIL2 (21, 22), which generate 3'-phosphate termini. Similarly, hPNKP is required to process termini generated by the topoisomerase I inhibitor camptothecin (23). Treatment with camptothecin stalls topoisomerase I while it is covalently attached to a 3'-phosphate group in the course of its nicking-resealing activity. The stalled enzyme can be cleaved from the DNA by Tdp1 leaving a strand break with 3'-phosphate and 5'-hydroxyl termini, which necessitates the subsequent action of PNKP. Down-regulation of hPNKP by RNAi, sensitized cells to a variety of genotoxic agents including ionizing radiation, camptothecin, methyl methanesulfonate and hydrogen peroxide (24). It remains to be determined which of hPNKP's activities, 5'-kinase or 3'-phosphatase (or both), is responsible for sensitization to each agent. The two activities are independent with separate DNA binding domains (25), but the phosphatase reaction appears to proceed ahead of the kinase reaction (26).

It is, therefore, desirable to identify synthetic lethal combinations, provide inhibitors of DNA repair proteins such as polynucleotide kinase/phosphatase, provide inhibitors of the synthetic lethal partners, and their compounds, compositions, methods and kits and uses thereof.

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

In accordance with an aspect of the present invention, there is provided compounds, compositions and methods for inducing synthetic lethality in a cancer cell(s).

In accordance with an aspect of the present invention, there is provided a method for the treatment of a subject having cancer, or suspected of having cancer, said cancer associated with a defect in PNKP, comprising: administering to said subject an inhibitor of a tumor suppressor.

In accordance with an aspect of the present invention, there is provided a method for the treatment of a subject having cancer, or suspected of having cancer, said cancer associated with a defect in PNKP, comprising: administering to said subject an inhibitor of ING3, CDKN3, PTPN6, PTEN or SMG1.

In accordance with an aspect of the present invention, there is provided a method of identifying a subject having cancer, or suspected of having cancer, that will benefit from treatment with an inhibitor of ING3, CDKN3, PTPN6, PTEN or SMG1, comprising: determining the presence of a defect in PNKP in a cancerous cell within said sample, wherein said defect reduces or abolishes the expression or activity of said PNKP, wherein a defect in said PNKP indicates said subject has a cancer which is suitable for treatment with said inhibitor of said ING3, CDKN3, PTPN6, PTEN or SMG1.

In accordance with an aspect of the present invention, there is provided a kit for the treatment of a subject having cancer, or suspected of having cancer, said cancer associated with a defect in PNKP, comprising: an inhibitor of ING3, CDKN3, PTPN6, PTEN or SMG1; and instructions for the use thereof.

In accordance with an aspect of the present invention, there is provided a kit for identifying a subject having cancer, or suspected of having cancer, that will benefit from treatment with an inhibitor of ING3, CDKN3, PTPN6, PTEN or SMG1, comprising: at least one reagent for determining the presence of a defect in PNKP in a cancerous cell within said sample, wherein said defect reduces or abolishes the expression or activity of said PNKP, wherein said defect in said PNKP indicates that said subject has a cancer which is suitable for treatment with said inhibitor of ING3, CDKN3, PTPN6, PTEN or SMG1; and instructions for the use thereof.

In accordance with an aspect of the present invention, there is provided a method for the treatment of a subject having cancer, or suspected of having cancer, said cancer associated with a defect in a tumour suppressor, comprising: administering to said subject an inhibitor PNKP.

In accordance with an aspect of the present invention, there is provided a method for the treatment of a subject having cancer, or suspect of having cancer, said cancer associated with a defect in ING3, CDKN3, PTPN6, PTEN, or SMG1, comprising: administering to said subject an inhibitor of PNKP.

In accordance with an aspect of the present invention, there is provided a method of identifying a subject having cancer, or suspected of having cancer, that will benefit from treatment with an inhibitor of PNKP, comprising: determining the presence of a defect in ING3, CDKN3, PTPN6, PTEN or SMG1 in a cancerous cell within said sample, wherein said defect reduces or abolishes the expression or activity of said ING3, CDKN3, PTPN6, PTEN or SMG1 wherein said defect in said ING3, CDKN3, PTPN6, PTEN, or SMG1 indicates that said subject has a cancer which is suitable for treatment with said inhibitor of said PNKP.

In accordance with an aspect of the present invention, there is provided a kit for the treatment of a subject having cancer, or suspected of having cancer, said cancer associated with a defect in ING3, CDKN3, PTPN6, PTEN or SMG1, comprising: an inhibitor of PNKP; and instructions for the use thereof.

In accordance with an aspect of the present invention, there is provided a kit for identifying a subject having cancer, or suspected of having cancer, that will benefit from treatment with an inhibitor of PNKP, comprising: at least one reagent for determining the presence of a defect in ING3, CDKN3, PTPN6, PTEN or SMG1 in a cancerous cell within said sample, wherein said defect reduces or abolishes the expression or activity of said ING3, CDKN3, PTPN6, PTEN, or SMG1 wherein a defect in said ING3, CDKN3, PTPN6, PTEN or SMG1 indicates that said subject has a cancer which is suitable for treatment with said inhibitor of PNKP.

In accordance with an aspect of the present invention, there is provided a use of an inhibitor of a tumour suppressor for the treatment of a subject having cancer, or suspected of having cancer, said cancer associated with a defect in PNKP.

In accordance with an aspect of the present invention, there is provided a use of an inhibitor of PNKP for the treatment of a subject having cancer, or suspect of having cancer, said cancer associated with a defect in ING3, CDKN3, PTPN6, PTEN, or SMG1.

In accordance with an aspect of the present invention, there is provided a compound or pharmaceutically acceptable salt thereof, comprising: (2R,4aR,7aS)-2-[(1R)-(1-hydroxyundecanyl)]-6-phenyl-1-[(4-nitrophenyl)amino]-4a,7a-dihydro-1H-pyrrolo[3,4-b]pyridine-5,7(2H,6H)-dione (H5); (2R,4aR,7aS)-2-[(1R)-1-hydroxypropyl]-6-phenyl-1-[(4-nitrophenyl)amino]-4a,7a-dihydro-1H-pyrrolo[3,4-b]pyridine-5,7(2H,6H)-dione (D5); {4-[(2R,4aR,7aS)-2-[(1R)-1-hydroxyundecanyl]-1-[(4-nitrophenyl)amino]-5,7-dioxo-1,2,4a,5,7,7a-hexahydro-6H-pyrrolo[3,4-b]pyridin-6-yl]phenyl}methanaminiumchloride (F15); (2R,4aR,7aS)-2-(1-hydroxymethyl)-6-phenyl-1-[(4-nitrophenyl)amino]-4a,7a-dihydro-1H-pyrrolo[3,4-b]pyridine-5,7(2H,6H)-dione (D7); or (2R,4aR,7aS)-2-[(1R)-(1-hydroxyundecanyl)]-6-(3,4,5-trimethoxyphenyl)-1-[(4-nitrophenyl)amino]-4a,7a-dihydro-1H-pyrrolo[3,4-b]pyridine-5,7(2H,6H)-dione (F8).

BRIEF DESCRIPTION OF THE DRAWINGS

Embodiments of the present invention will now be described, by way of example only, with reference to the attached Figures, wherein:

FIGS. 14A-14E depicts the siRNA target sequences (5'-3') of (A) PTEN, (B) ING3, (C) PTPN6, (D) CDKN3 and (E) SMG1;

FIG. 15 depicts chemical structure and name of inhibitors of PKNP;

FIG. 17A indicates 20-40 nM of two distinct siRNAs directed towards SHP-1 were used to transiently transfect both A549δPNKP and A549(Scramble) cell lines in a forward transfection. Both SHP-1 #5 (>5:1 ratio of survival) and SHP-1 #10 (~3.5:1 ratio of survival) were lethal only when combined with PNKP disruption. FIG. 17B depicts confirmation of the SHP-1/PNKP synthetic lethal relationship using MCF7 and MCF7δPNKP cells. The synthetic lethal associations identified in A549 were also evident to the same extent in MCF7 cells (Z-factor=−3.4, p<0.001);

FIG. 19A depicts a representative commet assay, FIG. 19B indicates, in the A549(Scramble) condition, repair to baseline levels of damage was completed between the 60-120 minute marks, however, FIG. 19C indicates repair in A549δPNKP cells was slightly retarded compared to control cells and still harbored some higher stage comets after 120 minutes. FIG. 19D indicates A549δSHP-1 cells showed higher basal level of DNA damage than control cells, as is evidenced by the higher proportion of stage 2 and greater comets, however these cells were able to repair DNA damage to baseline levels as efficiently as control cells;

FIGS. 20A-20C depict the incidence of DSBs using neutral single-cell gel electrophoresis (comet assay). Cells were plated 24 h in advance after which they were subjected to 5 Gy of γ-radiation. The cells were then allowed specific time periods for DNA repair to occur before being electrophoresed. FIG. 20A indicates DSBs in A549(Scramble) cells were mostly repaired by the 24 hour time point, however in FIG. 20B, the A549δPNKP cells showed severely retarded repair of DSBs. FIG. 20C indicates A549δSHP-1 cells had a higher basal level of DSBs;

FIG. 21A indicates cells transiently transfected with ASN control siRNA show only baseline levels of apoptotic and necrotic cells throughout all time points, however when cells are subjected to the apoptosis inducer BH3I-1, FIG. 21B indicates there is an increase in apoptotic cells beginning at 24 hours and continuing on through 72 hours. When A549-based cells lines are transiently transfected with SHP-1 depicted in FIG. 21C, there is an increase in apoptotic cells but not necrotic cells, however there is no increase in either apoptotic or necrotic cells when transfected with ASN;

Figure 1:
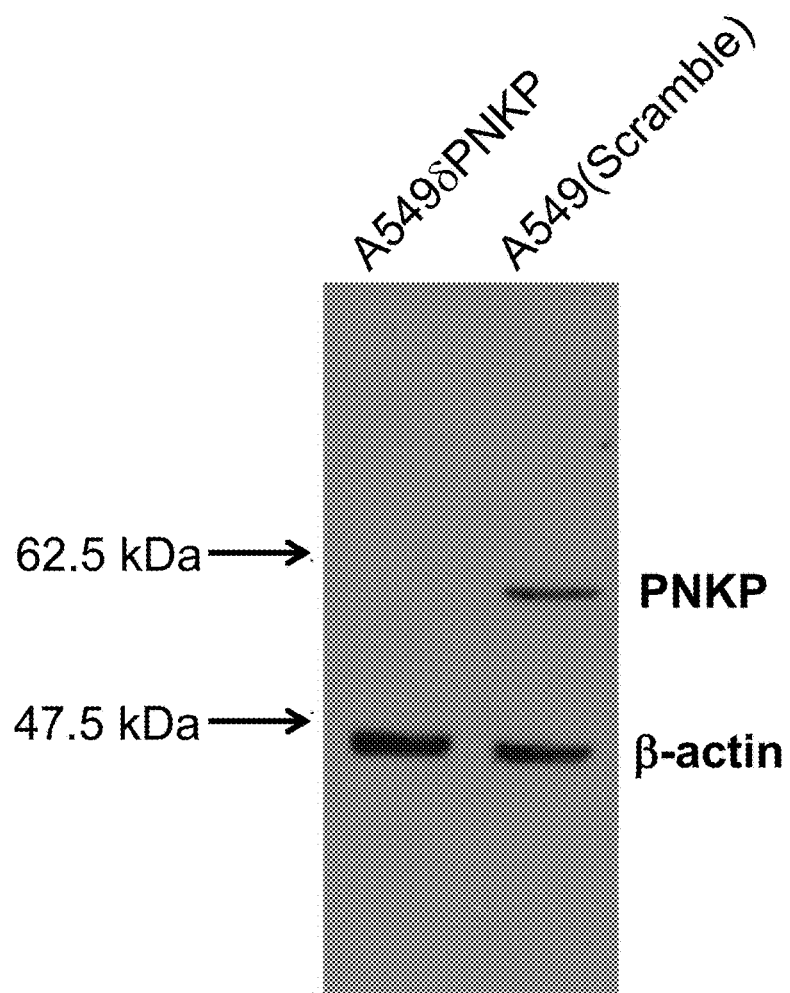
FIG. 1 is an immunoblot showing PNKP knockdown in A549 cells.

In the Detailed Description that follows, the numbers in bold face type serve to identify the component parts that are described and referred to in relation to the drawings depicting various embodiments of the invention. It should be noted that in describing various embodiments of the present invention, the same reference numerals have been used to identify the same of similar elements. Moreover, for the sake of simplicity, parts have been omitted from some figures of the drawings.

DETAILED DESCRIPTION

As will be described in more detail below, the present invention relates to compounds, compositions and methods for inducing synthetic lethality in a cancer cell(s).

Synthetic lethality arises when the combination of two non-essential protein disruptions in a single cell causes lethality. This phenomenon has been shown to occur between proteins involved in DNA repair and much attention has been focused on associations between PARP and BRCA.

As described herein, there is provided a synthetic lethal therapeutic strategy for the treatment or lessening the severity of a disorder, including those disorders arising in a subject with defects in a tumour suppressor(s), or with defects in PNKP. In one example the disorder is cancer.

In accordance with one aspect of the present invention, there is provided a method for the treatment of a subject having cancer, or suspected of having cancer, said cancer associated with a defect in PNKP, comprising: administering to said subject an inhibitor of a tumor suppressor. In one example, said inhibitor is an inhibitor of ING3, CDKN3, PTPN6, PTEN or SMG1.

In accordance with another aspect of the present invention, there is provided a method for the treatment of a subject having cancer, or suspected of having cancer, said cancer associated with a defect in PNKP, comprising: administering to said subject an inhibitor of ING3, CDKN3, PTPN6, PTEN or SMG1.

In accordance with another aspect of the present invention, there is provided a method of identifying a subject having cancer, or suspected of having cancer, that will benefit from treatment with an inhibitor of ING3, CDKN3, PTPN6, PTEN or SMG1, comprising: determining the presence of a defect in PNKP in a cancerous cell within said sample, wherein said defect reduces or abolishes the expression or activity of said PNKP, wherein a defect in said PNKP indicates said subject has a cancer which is suitable for treatment with said inhibitor of ING3, CDKN3, PTPN6, PTEN or SMG1.

In another aspect of the present invention there is provided a method for the treatment of a subject having cancer, or suspected of having cancer, said cancer associated with a defect in a tumour suppressor, comprising: administering to said subject an inhibitor PNKP. In one example, said tumour suppressor is ING3, CDKN3, PTPN6, PTEN, or SMG1.

In another aspect of the present invention there is provided a method for the treatment of a subject having cancer, or suspect of having cancer, said cancer associated with a defect in ING3, CDKN3, PTPN6, PTEN, or SMG1, comprising: administering to said subject an inhibitor of PNKP.

In another aspect of the present invention, there is provided a method of identifying a subject having cancer, or suspected of having cancer, that will benefit from treatment with an inhibitor of PNKP, comprising: determining the presence of a defect in ING3, CDKN3, PTPN6, PTEN or SMG1 in a cancerous cell within said sample, wherein said defect reduces or abolishes the expression or activity of said ING3, CDKN3, PTPN6, PTEN or SMG1, wherein said defect in said ING3, CDKN3, PTPN6, PTEN or SMG1 indicates that said subject has a cancer which is suitable for treatment with said inhibitor of said PNKP.

The term "subject" or "patient" as used herein, refers to any mammal or non-mammal that would benefit from the benefit from treatment. In certain examples a subject or patient includes, but is not limited to, humans, farm animals (such as cows, sheep, pigs and the like), companion animals (such as cats, dogs, horses and the like), primates and rodents (such as mice, rats and the like). In a specific example, the subject is a human.

The term "sample" as used herein encompasses a variety of cell-containing bodily fluids and/or secretions as well as tissues including, but not limited to, a cell(s), tissue, whole blood, blood-derived cells, plasma, serum, suptum, mucous, bodily discharge, and combinations thereof, and the like. Methods of obtaining such samples from a subject are known to the skilled worker.

Another embodiment of the present invention relates to treating or lessening the severity of one or more diseases in which PNKP plays a role. In one example, the disease is cancer.

A defect in PNKP is a PNKP deficient phenotype which may be deficient in a component of a PNKP mediated pathway, including but not limited to, expression of activity of a component of the pathway may be reduced or abolished in the cancer cell relative to control cells. In some embodiments, the cancer cell may be deficient in PNKP, for example, expression of activity of PNKP may be reduced or abolished in the cancer cell relative to control cells.

In accordance with an aspect of the present invention, there is provided a method for the treatment of a subject suffering from a disorder, such as cancer, associated with a defect in a tumour suppressor, comprising administering to said subject an inhibitor of PNKP. In a specific example, the defect in a tumour suppressor is a defect in ING3, CDKN3, PTPN6, PTEN and/or SMG1.

As used herein, the term "tumour suppressor" includes known tumour suppressors, and implicated or suspected as a tumour suppressor. Examples of tumour suppressors include, but are not limited to ING3, CDKN3, PTPN6, and PTEN. An example of an implicated tumour suppressor includes, but is not limited to, SMG1.

The term "cancer" as used herein, refers to or describes the physiological condition in a mammal that is typically characterized by unregulated cell growth. Cancers may be solid or non-solid cancers. Cancers may be a primary cancer and/or metastatic cancer. Cancers include, but are not limited to, a solid cancer, a non-solid cancer, a primary cancer, a metastatic cancer, breast cancer, uterine cancer, ovarian cancer, prostate cancer, lung cancer, colorectal cancer, cervical cancer, liver cancer, head and neck cancer, oesophageal cancer, pancreatic cancer, renal cancer, stomach cancer and cerebral cancer, lymphoma, NK lymphoma, T cell lymphoma, leukemia, lymphoid malignancies, sarcomas, carcinomas skin cancer, bladder cancer, a carcinoma, a melanoma, endometrial carcinoma, astrocytoma, malignant astrocytoma, colorectal cancer, familial cancer, or sporadic cancer.

ING3

A defect in ING3 is a ING3 deficient phenotype which may be deficient in a component of a ING3 mediated pathway i.e., expression of activity of a component of the pathway may be reduced or abolished in the cancer cell relative to control cells. In some embodiments, the cancer cell may be deficient in ING3 i.e., expression of activity of ING3 may be reduced or abolished in the cancer cell relative to control cells.

Dysregulation of apoptosis also contributes to a variety of human diseases, such as cancer and autoimmune diseases. ING family proteins (ING1-ING5) are involved in many cellular processes, and appear to play a significant role in apoptosis. ING3 has been shown to help control cell cycle, apoptosis and modulate transcription, and displays irregular expression in human head and neck cancer and reduced expression in melanoma. Loss or downregulation of ING protein function is frequently observed in different tumour types. The mechanism of diminished ING3 expression in melanoma is not clear. ING3 has been implicated in bladder cancer, head and neck cancer, squamous cell carcinoma, lymphoma and melanoma. Although the mechanisms of action are unclear, in melanoma ING3 has been reported to undergo degradation through the ubiquitin-proteasome pathway.

CDKN3 (Also Referred to as KAP)

A defect in CDKN3 is a CDKN3 deficient phenotype which may be deficient in a component of a CDKN3 mediated pathway i.e., expression of activity of a component of the pathway may be reduced or abolished in the cancer cell relative to control cells. In some embodiments, the cancer cell may be deficient in CDKN3 i.e., expression of activity of CDKN3 may be reduced or abolished in the cancer cell relative to control cells.

CDKN3 (cyclin-dependent kinase inhibitor 3) encodes the protein KAP, which is a human dual specificity protein I phosphatase that was identified as a cyclin-dependent kinase inhibitor, and has been shown to interact with and dephosphorylate CDK2 kinase and thus prevent the activation of CDK2 kinase. The gene has been reported to be deleted, mutated, or overexpressed in several kinds of cancers. CDKN3 has been reported as an overexpressed gene in breast and prostate cancer by using a phosphatase domain-specific differential-display PCR strategy. KAP is reduced in some forms of malignant astrocytomas. CDKN3 has also been implicated in lung cancer. It has been reported that in normal cells, CDKN3 protein is primarily found in the perinuclear region, but in tumour cells, a significant portion of the protein is found in the cytoplasm.

PTPN6 (Also Known as SHP-1)

A defect in PTPN6 is a PTPN6 deficient phenotype which may be deficient in a component of a PTPN6 mediated pathway i.e., expression of activity of a component of the pathway may be reduced or abolished in the cancer cell relative to control cells. In some embodiments, the cancer cell may be deficient in PTPN6 i.e., expression of activity of PTPN6 may be reduced or abolished in the cancer cell relative to control cells.

PTPN6, an SH2 domain-containing protein tyrosine phosphatase, has been reported as being expressed in hematopoietic cells and behaves as a regulator controlling intracellular phosphotyrosine levels in lymphocytes. PTPN6 has been proposed as a candidate tumor suppressor gene in lymphoma, leukemia and other cancers, as it functions as an antagonist to the growth-promoting and oncogenic potentials of tyrosine kinase. PTPN6 protein has been reported as normally or over-expressed in some non-lymphocytic cell lines, such as prostate cancer, ovarian cancer and breast cancer cell lines. PTPN6 expression is also reported as decreased in some breast cancer cell lines with negative expression of estrogen receptor as well as some prostate and colorectal cancer cell lines. PTPN6 has been implicated in a variety of cancers, including lymphoma, leukemia, prostate cancer, ovarian cancer, breast cancer, NK lymphoma, T cell lymphoma, or colorectal cancer.

PTPN6 expression was shown to be diminished or absent in 40/45 malignant prostate tissues, 95% of various malignant lymphomas and 100% of NK and T cell lymphomas. PTN6 protein and mRNA have been reported to be diminished or abolished in most of the cancer cell lines and tissues examined. Similarly, growth of cancer cells was reported as being suppressed after introducing the PTN6 gene into the corresponding cell lines.

PTEN

A defect in PTEN is a PTEN deficient phenotype which may be deficient in a component of a PTEN mediated pathway i.e., expression of activity of a component of the pathway may be reduced or abolished in the cancer cell relative to control cells. In some embodiments, the cancer cell may be deficient in PTEN i.e., expression of activity of PTEN may be reduced or abolished in the cancer cell relative to control cells.

PTEN is a tumour suppressor encoding a phosphatase.

PTEN is one of the most frequently mutated or deleted genes in inherited and sporadic human cancers, including breast cancer. Deletion or inactivation of PTEN has also been reported in glioblastoma, endometrial carcinoma, and lymphoid malignancies. PTEN downregulation has been found in leukemia cells.

SMG1

A defect in SMG1 is a SMG1 deficient phenotype which may be deficient in a component of a SMG1 mediated pathway i.e., expression of activity of a component of the pathway may be reduced or abolished in the cancer cell relative to control cells. In some embodiments, the cancer cell may be deficient in SMG1 i.e., expression of activity of SMG1 may be reduced or abolished in the cancer cell relative to control cells.

SMG1 protein is involved in nonsense-mediated mRNA decay (NMD) as part of the mRNA surveillance complex. The protein has kinase activity and is thought to function in NMD by phosphorylating the regulator of nonsense transcripts 1 protein.

From the foregoing it will be clear that the name of the gene and corresponding gene product (i.e. the corresponding protein encode by the gene) are used interchangeably herein. For example, the SHP-1 protein is encoded by the PTPN6 gene and the KAP protein is encoded by the CDKN3 gene.

In another specific example, the compounds, compositions and methods are suitable to treatment of carcinoma. In another specific example, the cancer is lung carcinoma. In another specific example the cancer is breast carcinoma.

In some examples, a "defect" includes, sequence variations, such as mutations and polymorphisms, which reduce or abolish the expression or activity. Sequence variations may include a deletion, insertion or substitution of one or more nucleotides, relative to the wild-type nucleotide sequence, a gene amplification or an increase or decrease in methylation, for example hypermethylation. Sequence variations may be in a coding or non-coding region of the nucleic acid sequence. Mutations in the coding region of the gene encoding the component may prevent the translation of full-length active protein i.e. truncating mutations, or allow the translation of full-length but inactive or impaired function protein i.e. mis-sense mutations. Mutations or epigenetic changes, such as methylation, in non-coding regions of the gene encoding the component, for example, in a regulatory element, may prevent transcription of the gene. A nucleic acid comprising one or more sequence variations may encode a variant polypeptide which has reduced or abolished activity or may encode a wild-type polypeptide which has little or no expression within the cell, for example through the altered activity of a regulatory element. A nucleic acid comprising one or more sequence variations may have one or more mutations or polymorphisms relative to the wild-type sequence.

Determination of the presence of a defect, such as a sequence variation in a nucleic acid may be accomplished by detecting the presence of the variant nucleic acid sequence in one or more cells of a test sample or by detecting the presence of the variant polypeptide which is encoded by the nucleic acid sequence. Non-limiting example of sequence variation detection allele specific amplification, OLA, ALEX, COPS, Taqman, Molecular Beacons, RFLP, and restriction site based PCR and FRET techniques.

Determination of the presence of a defect, such as a sequence variation in a polypeptide, may be accomplished using polypeptide sequence variation techniques including, but not limited to immunoassays.

Determination of a Defect, for Example the Detection of Sequence Variation, Typically Requires a Discrimination Technique, Optionally an Amplification Reaction and Optionally a Signal Generation System.

In some examples, nucleic acid or an amplified region thereof may be sequenced to identify or determine the presence of polymorphism or mutation therein. A polymorphism or mutation may be identified by comparing the sequence obtained with the known sequence of the component of the tumour suppressor or PNKP-mediated cellular pathway, for example as set out in sequence databases. Alternatively, it can be compared to the sequence of the corresponding nucleic acid from normal cells. In particular, the presence of one or more polymorphisms or mutations that cause abrogation or loss of function may be determined.

Sequencing may be performed using any one of a range of standard techniques. Having sequenced nucleic acid of an individual or sample, the sequence information can be retained and subsequently searched without recourse to the original nucleic acid itself. Thus, for example, scanning a database of sequence information using sequence analysis software may identify a sequence alteration or mutation.

In some examples, the determination of a defect includes determining the presence of one or more variations in a nucleic acid may comprise hybridising one or more (e.g. two) oligonucleotides to nucleic acid obtained from a sample, for example genomic DNA, RNA or cDNA. Where the nucleic acid is double-stranded DNA, hybridisation will generally be preceded by denaturation to produce single-stranded DNA. The hybridisation may be as part of a PCR procedure, or as part of a probing procedure not involving PCR.

By the terms "treating" or "lessening the severity", it is to be understood that any reduction using the methods, compounds and composition disclosed herein, is to be considered encompassed by the invention. Treating or lessening in severity, may, in one embodiment comprise enhancement of survival, or in another embodiment, halting disease progression, or in another embodiment, delay in disease progression, or in another embodiment, diminishment of pain, or in another embodiment, delay in disease spread to alternate sites, organs or systems. Treating or lessening of severity includes amelioration or palliation of the disease state, and remission or improved prognosis. Treating or lessening in severity, may, in one embodiment, comprise a reduction in the amount/dosage of radiotherapy and/or chemotherapy otherwise required to treat a subject, thereby resulting in a reduction of normal tissue damage. It is to be understood that any clinically beneficial effect that arises from the methods, compounds and compositions disclosed herein, is considered to be encompassed by the invention.

In a specific example, treatment is carried out in vivo.

In a specific example, treatment is carried out in vitro, including but not limited to, in test tube, in cultured cells (both adherent cells and non-adherent cells), and the like.

In a specific example, treatment is carried out ex vivo, including but not limited to, in test tube, in cultured cells (both adherent cells and non-adherent cells), and the like.

The term "prognosis" as used herein refers to the prediction of the likelihood of cancer-attributable death or progression, including recurrence, metastatic spread, and drug resistance, of a neoplastic disease.

The term "subject" or "patient" as used herein, refers to any mammal or non-mammal that would benefit from determining the benefit from treatment. In certain examples a subject or patient includes, but is not limited to, mammals such as humans, farm animals (pigs, cow, sheep, and the like), companion animals (such as cats, dogs, horses, rabbits, and the like), primates and rodent (such as mice and rats, and the like). In a specific embodiment, the subject is a human.

Inhibitors of PNKP include, but are not limited to, RNA interference molecules, small molecules, nucleic acids, antibodies, peptides, and/or aptamers.

The term "antibodies" refers to any specific binding member having an antibody antigen-binding member or substance having an antibody antigen-binding domain with the required specificity. The term encompasses antibody fragments and derivatives, any polypeptide comprising an immunoglobulin binding domain, which is natural or wholly synthetic or partially synthetic. Chimeric molecules comprising an immunoglobulin binding domain, or equivalent, fused to another polypeptide are included. Examples of antibodies include both monoclonal and polyclonal antibodies.

Inhibitors of tumour suppressors, including inhibitors of ING3, SMG1, CDKN3, PTPN6, and PTEN, include, but are not limited to, RNA interference molecules, small molecules, nucleic acids, antibodies (both monoclonal and polyclonal), peptides, and/or aptamers.

Examples of RNA interference molecules include a RNAi molecule, a siRNA molecule, or a shRNA molecule.

In one example, expression of PNKP and/or tumour suppressors, including ING3, CDKN3, PTPN6, PTEN and/or SMG1, may be inhibited using anti-sense or RNAi technology. The use of these approaches to down-regulate gene expression and/or protein activity is known to the skilled worker.

Anti-sense oligonucleotides may be designed to hybridise to the complementary sequence of nucleic acid, pre-mRNA or mature mRNA, interfering with the production of the PNKP and tumour suppressors including ING3, CDKN3, PTPN6, PTEN and/or SMG1 so that its expression is reduced or completely or substantially prevented. In addition to targeting coding sequence, anti-sense techniques may be used to target control sequences of a gene, e.g. in the 5' flanking sequence, whereby the anti-sense oligonucleotides can interfere with expression control sequences.

Oligonucleotides may be generated in vitro or ex vivo for administration or anti-sense RNA may be generated in vivo within cells in which down-regulation is desired. Thus, double-stranded DNA may be placed under the control of a promoter in a "reverse orientation" such that transcription of the anti-sense strand of the DNA yields RNA which is complementary to normal mRNA transcribed from the sense strand of the target gene. The complementary anti-sense RNA sequence is thought then to bind with mRNA to form a duplex, inhibiting translation of the endogenous mRNA from the target gene into protein.

The complete sequence corresponding to the coding sequence in reverse orientation need not be used. For example, fragments of sufficient length may be used. It is a routine matter for the person skilled in the art to screen fragments of various sizes and from various parts of the coding or flanking sequences of a gene to optimize the level of anti-sense inhibition. It may be advantageous to include the initiating methionine ATG codon, and perhaps one or more nucleotides upstream of the initiating codon.

A suitable fragment may be determined by the skilled worker.

An alternative to anti-sense is to use a copy of all or part of the target gene inserted in sense, that is the same, orientation as the target gene, to achieve reduction in expression of the target gene by co-suppression.

Double stranded RNA (dsRNA) has been found to be even more effective in gene silencing than either sense or antisense strands alone. dsRNA mediated silencing is gene specific and is often termed RNA interference (RNAi). Methods relating to the use of RNAi to silence genes are known in the art.

RNA interference is a two-step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction.

RNAi may also be efficiently induced using chemically synthesized siRNA duplexes of the same structure with 3'-overhang ends. Synthetic siRNA duplexes have been shown to specifically suppress expression of endogenous and heterologous genes in a wide range of mammalian cell lines.

Another possibility is that nucleic acid is used which on transcription produces a ribozyme, able to cut nucleic acid at a specific site and therefore also useful in influencing gene expression.

Small RNA molecules may be employed to regulate gene expression. These include targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

A role for the RNAi machinery and small RNAs in targeting of heterochromatin complexes and epigenetic gene silencing at specific chromosomal loci has also been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA.

In the art, these RNA sequences are termed "short or small interfering RNAs" (siRNAs) or "microRNAs" (miRNAs) depending in their origin. Both types of sequence may be used to down-regulate gene expression by binding to complimentary RNAs and either triggering mRNA elimination (RNAi) or arresting mRNA translation into protein. siRNA are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully-complementary sequences.

The siRNA ligands are typically double stranded and, in order to optimize the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments employing double-stranded siRNA, the molecule may have symmetric 3' overhangs, e.g. of one or two (ribo) nucleotides, typically a UU of dTdT 3' overhang. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs. The longer dsRNA molecule may have symmetric 3' or 5' overhangs, e.g. of one or two (ribo) nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length.

Another alternative is the expression of a short hairpin RNA molecule (shRNA) in the cell. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter.

Alternatively, the shRNA may be synthesised exogenously (in vitro) by transcription from a vector. The shRNA may then be introduced directly into the cell. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific promoter. In a further embodiment, the siRNA, longer dsRNA or miRNA is produced exogenously (in vitro) by transcription from a vector.

Alternatively, siRNA molecules may be synthesized using standard solid or solution phase synthesis techniques which are known in the art. Linkages between nucleotides may be phosphodiester bonds or alternatives, e.g., linking groups of the formula P(O)S, (thioate); P(S)S, (dithioate); P(O)NR'2; P(O)R1; P(O)OR5; CO; or CONR 12 wherein R is H (or a salt) or alkyl (1-12C) and R6 is alkyl (1-9C) is joined to adjacent nucleotides through —O— or —S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-0-alkyl; 2-0-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetyl cytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethyl guanine, 2-methyladenine, 2-methylguanine, 3-methyl cytosine, 5-methyl cytosine, N6-methyladenine, 7-methyl guanine, 5-methylaminomethyl uracil, 5-methoxy amino methyl-2-thiouracil, -D-mannosylqueosine, 5-methoxycarbonylmethyluracil, 5-methoxyuracil, 2 methyl thio-N6-isopentenyladenine, uracil-5-oxyacetic acid methyl ester, psueouracil, 2-thiocytosine, 5-methyl-2 thiouracil, 2-thiouracil, 4-thiouracil, 5-methyluracil, N-uracil-5-oxyacetic acid methylester, uracil 5-oxyacetic acid, queosine, 2-thiocytosine, 5-propyluracil, 5-propyl cytosine, 5-ethyluracil, 5-ethyl cytosine, 5-butyluracil, 5-pentyluracil, 5-pentylcytosine, and 2,6,diaminopurine, methylpsuedouracil, 1-methyl guanine, 1-methylcytosine.

In another example, expression of PNKP and/or tumour suppressors including ING3, CDKN3, PTPN6, PTEN and/or SMG1, may be inhibited using inhibitors/inhibitory compounds and compositions. Such compounds and compositions to down-regulate gene expression and/or protein activity are known to the skilled worker.

Small molecule inhibitors of CDKN3 include, but are not limited to, orthovanadate, iodoacetic acid, N-ethylmaleimide, roscovitine, or olomoucine.

Small molecule inhibitors of PTPN6 include, but are not limited to, TPI-1, NSC-87877 or sodium stibogluconate.

Small molecule inhibitors of PTEN include, but are not limited to, bisperoxovan compounds, potassium bisperoxo (1,10-phenanthroline)oxovanadate (bpV(phen)); vanadyl hydroxypicolinic acid 5-hydroxypyridine-2-carboxyl (VO-OHpic); 3-phosphorothioate-PtdIns(3,4,5)P3 (3-PT-PIP3); or wortmannin.

Small molecule inhibitors of SMG1 include, but are not limited to, wortmannin or caffeine.

Small molecule inhibitors of PKNP include, but are not limited to, the compounds in FIG. 15, including: 2-(1- hydroxyundecyl)-1-(4-nitrophenylamino)-6-phenyl-6,7a-dihydro-1H-pyrrolo[3,4-b]pyridine-5,7(2H,4aH)-dione (A12B4C3); 2-(hydroxy(phenyl)methyl)-1-(4-nitrophenylamino)-6-phenyl-6,7a-dihydro-1H-pyrrolo[3,4-b]pyridine-5,7(2H,4aH)-dione (A1B4C3); 2-(hydroxy(3,4,5-trimethoxyphenyl)methyl)-1-(4-nitrophenylamino)-6-phenyl-6,7a-dihydro-1H-pyrrolo[3,4-b]pyridine-5,7(2H,4aH)-dione (A6B4C3); tert-butyl 2-(1-hydroxy-2,2-diphenylethyl)-6-methyl-5,7-dioxo-2,4a,5,6,7,7a-hexahydro-1H-pyrrolo[3,4-b]pyridin-1-ylcarbamate (A26B11C2); or 2-(hydroxy(thiophen-2-yl)methyl)-6-methy 1-1-(phenylamino)-6,7a-dihydro-1H-pyrrolo[3,4-b]pyridine-5,7(2H,4aH)-dione (A39B1C2).

Figure 33:
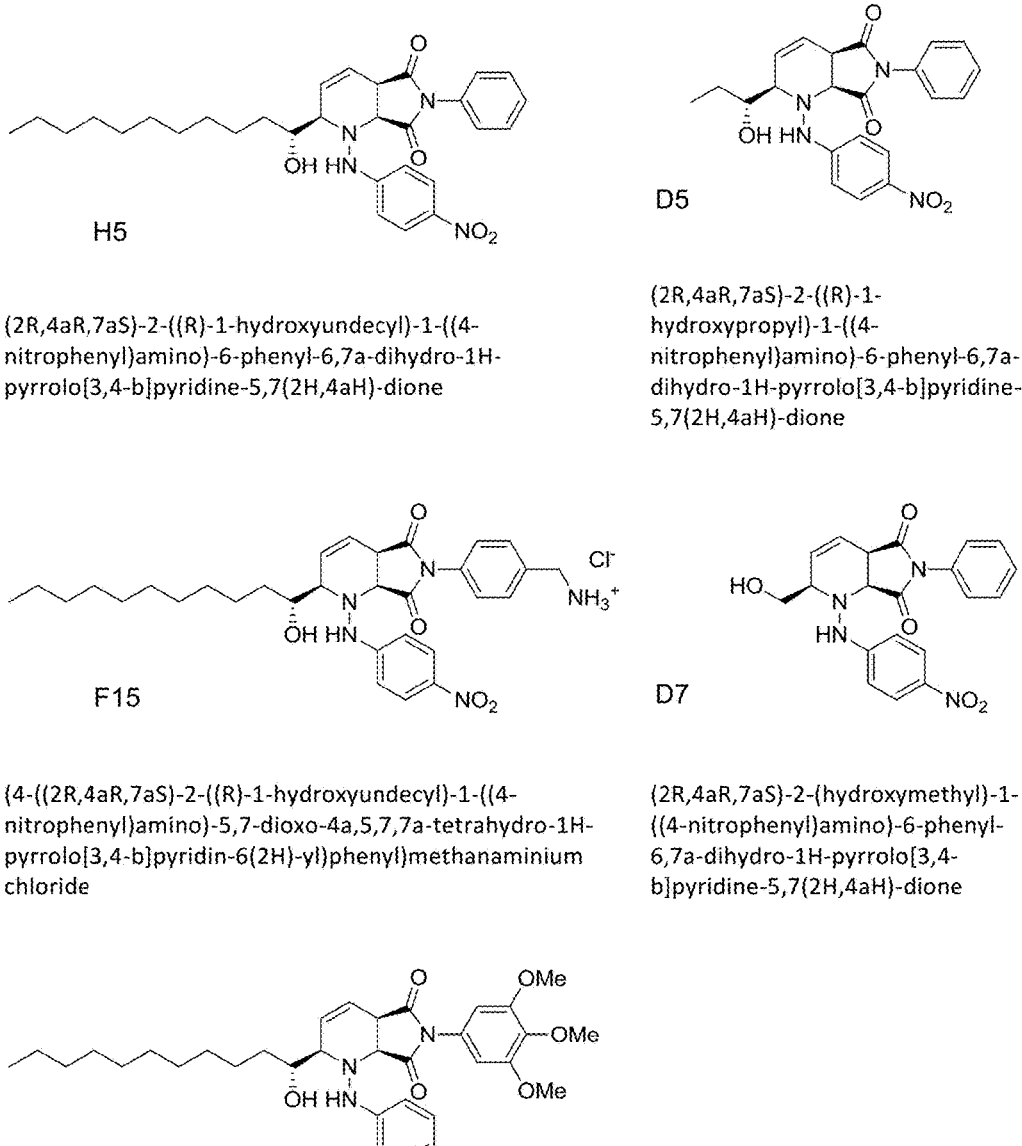
FIG. 33 depicts chemical structure and name of inhibitors of PKNP.

Additional small molecule inhibitors of PNKP include the compounds in FIG. 33, including, (2R,4aR,7aS)-2-[(1R)-(1-hydroxyundecanyl)]-6-phenyl-1-[(4-nitrophenyl)amino]-4a,7a-dihydro-1H-pyrrolo[3,4-b]pyridine-5,7(2H,6H)-dione (H5); (2R,4aR,7aS)-2-[(1R)-1-hydroxypropyl]-6-phenyl-1-[(4-nitrophenyl)amino]-4a,7a-dihydro-1H-pyrrolo[3,4-b]pyridine-5,7(2H,6H)-dione (D5); {4-[(2R,4aR,7aS)-2-[(1R)-1-hydroxyundecanyl]-1-[(4-nitrophenyl)amino]-5,7-dioxo-1,2,4a,5,7,7a-hexahydro-6H-pyrrolo[3,4-b]pyridin-6-yl]phenyl}methanaminium chloride (F15); (2R,4aR,7aS)-2-(1-hydroxymethyl)-6-phenyl-1-[(4-nitrophenyl)amino]-4a,7a-dihydro-1H-pyrrolo[3,4-b]pyridine-5,7(2H,6H)-dione (D7); (2R,4aR,7aS)-2-[(1R)-(1-hydroxyundecanyl)]-6-(3,4,5-trimethoxyphenyl)-1-[(4-nitrophenyl)amino]-4a,7a-dihydro-1H-pyrrolo[3,4-b]pyridine-5,7(2H,6H)-dione (F8).

In another example, the inhibitory compounds and/or compositions are provided in a pharmaceutically effective amount.

The term "pharmaceutically effective amount" as used herein refers to the amount of a drug or pharmaceutical agent that will elicit the biological or medical response of a tissue, system, animal or human that is being sought by a researcher or clinician. This amount can be a therapeutically effective amount.

The compounds and compositions are provided in a pharmaceutically acceptable form.

The term "pharmaceutically acceptable" as used herein includes compounds, materials, compositions, and/or dosage forms which are suitable for use in contact with the tissues of a subject (e.g. human) without excessive toxicity, irritation, allergic response, or other problem or complication, commensurate with a reasonable benefit/risk ratio. Each carrier, excipient, etc. is also "acceptable" in the sense of being compatible with the other ingredients of the formulation.

The active compounds and compositions are for administration to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

A compound or composition may be administered alone or in combination with other treatments, either simultaneously or sequentially, dependent upon the condition to be treated.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

The compounds and compositions may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot/for example, subcutaneously or intramuscularly.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection.

The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising agents disclosed herein may be used in the methods described herein in combination with standard chemotherapeutic regimes or in conjunction with radiotherapy.

Methods of the invention are conveniently practiced by providing the compounds and/or compositions used in such method in the form of a kit. Such a kit preferably contains the composition. Such a kit preferably contains instructions for the use thereof.

In one aspect of the present invention, there is provided a kit for the treatment of a subject having cancer, or suspected of having cancer, said cancer associated with a defect in PNKP, comprising: an inhibitor of ING3, CDKN3, PTPN6, PTEN or SMG1; and instructions for the use thereof In one aspect of the present invention, there is provided a kit for identifying a subject having cancer, or suspected of having cancer, that will benefit from treatment with an inhibitor of ING3, CDKN3, PTPN6, PTEN or SMG1, comprising: at least one reagent for determining the presence of a defect in PNKP in a cancerous cell within said sample, wherein said defect reduces or abolishes the expression or activity of said PNKP, wherein said defect in said PNKP indicates that said subject has a cancer which is suitable for treatment with said inhibitor of ING3, CDKN3, PTPN6, PTEN or SMG1; and instructions for the use thereof.

In one aspect of the present invention, there is provided a kit for the treatment of a subject having cancer, or suspected of having cancer, said cancer associated with a defect in ING3, CDKN3, PTPN6, PTEN, or SMG1 comprising: an inhibitor of PNKP; and instructions for the use thereof.

In one aspect of the present invention, there is provided a kit for identifying a subject having cancer, or suspected of having cancer, that will benefit from treatment with an inhibitor of an inhibitor of PNKP, comprising: at least one reagent for determining the presence of a defect in ING3, CDKN3, PTPN6, PTEN or SMG1 in a cancerous cell within said sample, wherein said defect reduces or abolishes the expression or activity of said ING3, CDKN3, PTPN6, PTEN or SMG1, wherein a defect in said ING3, CDKN3, PTPN6, PTEN or SMG1 indicates that said subject has a cancer which is suitable for treatment with said inhibitor of PNKP.

To gain a better understanding of the invention described herein, the following examples are set forth. It should be understood that these examples are for illustrative purposes only. Therefore, they should not limit the scope of this invention in anyway.

EXAMPLES

Example—1

Materials and Methods for Determining Synthetically Lethal Associations with Polynucleotide Kinase (PNKP)

Cells

A549 (human lung carcinoma cells) and MCF7 (human breast adenocarcinoma cells) were obtained from the American Type Culture Collection (Manassas, Va.), and were cultured at 37° C. and 5% $CO_2$ in a humidified incubator in a 1:1 mixture of Dulbecco's Modified Eagle's Medium and F12 (DMEM/F12) supplemented with 10% fetal bovine serum (FBS), penicillin (50 U/mL), streptomycin (50 μg/mL), L-glutamine (2 mM), non-essential amino acids (0.1 mM) and sodium pyruvate (1 mM). All culture supplements were purchased from Invitrogen.

A549δPNKP (A549 stably depleted of PNKP) were generated using the following protocol. On day 1, 20,000 A549 cells were plated in a 24-well dish in 1 mL DMEM/F12 without antibiotics and allowed to adhere overnight in a humidified incubator at 37° C. The following day, 1 μg of pSUPER.neo plasmid DNA containing an shRNA sequence (5'-AGAGATGACGGACTCCTCT-3') (SEQ ID NO:1) directed to nucleotides 1391-1410 of the PNKP cDNA was incubated for five minutes at room temperature in 100 μL of Opti-MEM. Simultaneously, 6 μL of Lipofectamine 2000 was incubated with 100 μL of Opti-MEM at room temperature for five minutes. After the five-minute incubation, transfection complexes were allowed to form by gently combining the plasmid DNA and Lipofectamine 2000 dilutions for 20 minutes at room temperature. The media was aspirated off the cells and 100 μL, of the transfection complexes was then added to the well and allowed to incubate for 24 hours at 37° C. The following day, the cells were trypsinized and split evenly into 10×100 mm dishes containing DMEM/F12 without antibiotics. The next day, the media was aspirated and replaced using DMEM/F12 with antibiotics+650 μg/mL G418 to select for positive transfectants. Cells grew under selection for 7 days (media was replaced every 3 days fresh media+G418), after which the selective drug was removed. Colonies were allowed to form for ~14 days, and single colonies were picked, expanded and tested for PNKP expression using western blotting.

MCF7δPNKP cells were generated using a protocol similar to the one used to generate A549δPNKP. However, 24-well dishes were seeded to ~70% confluency the day prior to transfection, and selection was done using 350 μg/mL G418.

Generating Cell Lysate and Western Blotting

Approximately $8 \times 10^5$ cells were washed twice with ice cold PBS and resuspended in CHAPS buffer (0.5% CHAPS, 137 mM NaCl, 50 mM Tris-HCl pH 7.5, and 1 mM EDTA). Cells were then rocked for 1 hour at 4° C., after which cell debris was spun down at 14,000 rpm for 20 minutes at 4° C. Determination of whole cell lysate concentration was then done using the Bradford Assay. 50 μg of protein was added to 1× sample buffer and was boiled for 5 minutes. Samples were then separated by 10% SDS-PAGE (200V for 50 minutes at room temperature) and transferred to a nitrocellulose membrane by wet transfer (100V for 1 hour at 4° C.). Membranes were then blocked in 5% PBSMT (PBS, 5% milk powder, 0.1% Tween 20) for 1 hour at room temperature. Monoclonal primary antibodies were incubated on the membrane at a 1:2500 dilution in 5% PBSMT overnight at 4° C. Polyclonal primary antibodies were incubated at a 1:5000 dilution in 5% PBSMT overnight at 4° C. Membranes then underwent 5×10 minute washes in PBST, and then were incubated with the appropriate HRP-conjugated secondary antibody at a 1:5000 dilution in 5% PBSMT for 30 minutes at room temperature. Membranes were then washed 6×5 minutes in PBST. Membranes were then incubated with 2 mL total of Lumi-Light Western Blotting substrate (Roche) for 5 minutes and then underwent autoradiography.

Proliferation Assay (for Screening)

2500-3500 cells were plated per well in a 96-well plate using the JANUS Automated Workstation (PerkinElmer), and allowed 24 hours to adhere in a humidified incubator at 37° C. and 5% $CO_2$. 2 μM final concentration of siRNA was added to Opti-MEM at the same time as a 1:25 dilution of Dharmafect Transfection 1 was allowed to incubate at room temperature for 5 minutes. The two solutions were then combined and transfection complexes were allowed to form at room temperature for 20 minutes. The media was then aspirated from the cells and 100 μL of the transfection complexes was added per well and the plate was incubated at 37° C. and 5% $CO_2$ for 72 hours. After 72 hours, a 440 μM Resazurin sodium salt (Sigma) dilution was added to final concentration of 10% v/v and incubated at 37° C. and 5% $CO_2$ for 50-90 minutes. Resazurin is normally non-fluorescent and is reduced to the fluorescent compound, resorufin, in metabolically active cells. Cell viability was read with a FLUOstar Optima® plate reader (BMG Labtec Inc. Durham, N.C.) using a 540 nm excitation filter and a 590 nm emission filter.

Proliferation Assay (for Verification)

2500-3500 cells were plated per well in a 96-well dish with all wells surrounding samples filled with 100 μL ddH$_2$O and left for 24 hours. 16 nM final siRNA concentration (PTEN, PTPN6 and CDKN3) or 32 nM final siRNA concentration (SMG1 and ING3) complexed with Dharmafect 1 transfection reagent was added to cells in DMEM/F12 without penicillin and streptomycin. The drug or siRNA were then left to incubate with the cells for a total of 72 hours at 37° C. and 5% CO$_2$. After 72 hours, a 440 M Resazurin sodium salt (Sigma) dilution was added to final concentration of 10% and incubated at 37° C. and 5% CO$_2$ for 50 minutes. The samples' fluorescence was then read with a FLUOstar Optima® plate reader (BMG Labtec Inc. Durham, N.C.) using a 540 nm excitation filter and a 590 nm emission filter.

Discussion—I

A siRNA library screen of Qiagen's druggable genome was performed to identify synthetically lethal associations between polynucleotide kinase/phosphatase (PNKP) and proteins non-DNA repair. The screen was done in duplicate using the lung carcinoma cell line A549, stably depleted of PNKP using shRNA (A549δPNKP) and then again in duplicate using A549 stably expressing a scrambled shRNA (13-6) as a control.

FIG. 1 is an immunoblot showing PNKP knockdown in A549 cells.

Figure 2:
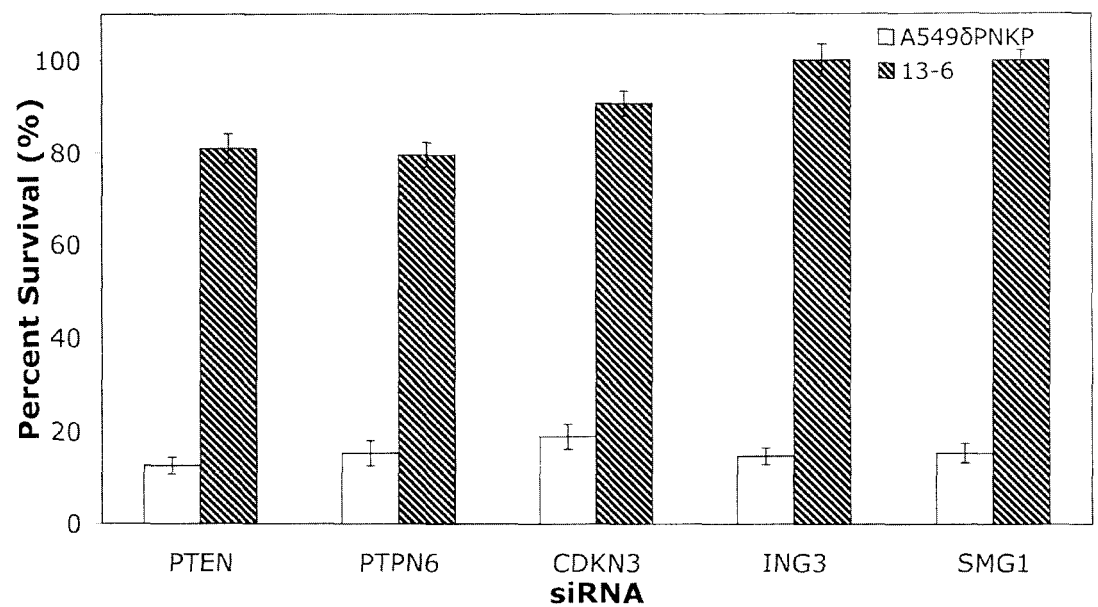
FIG. 2 is a bar graph depicting synthetic lethality between PNKP and selected hits from siRNA Screen.
Figure 3:
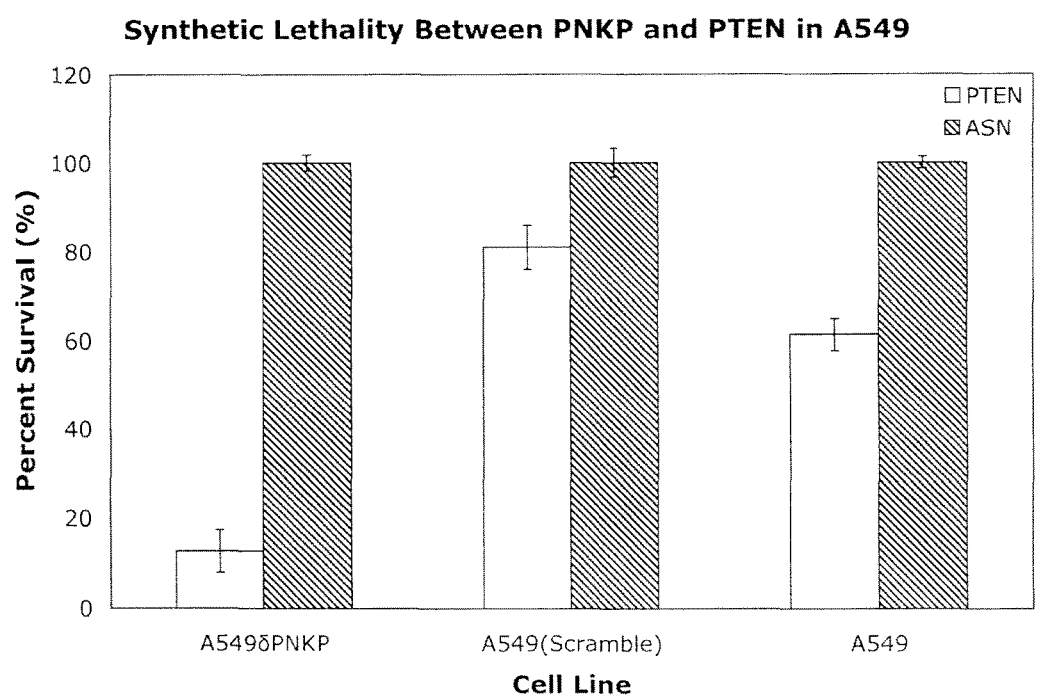
FIG. 3 is a bar graph depicting synthetic lethality between PKNP and PTEN in A549 cells.
Figure 4:
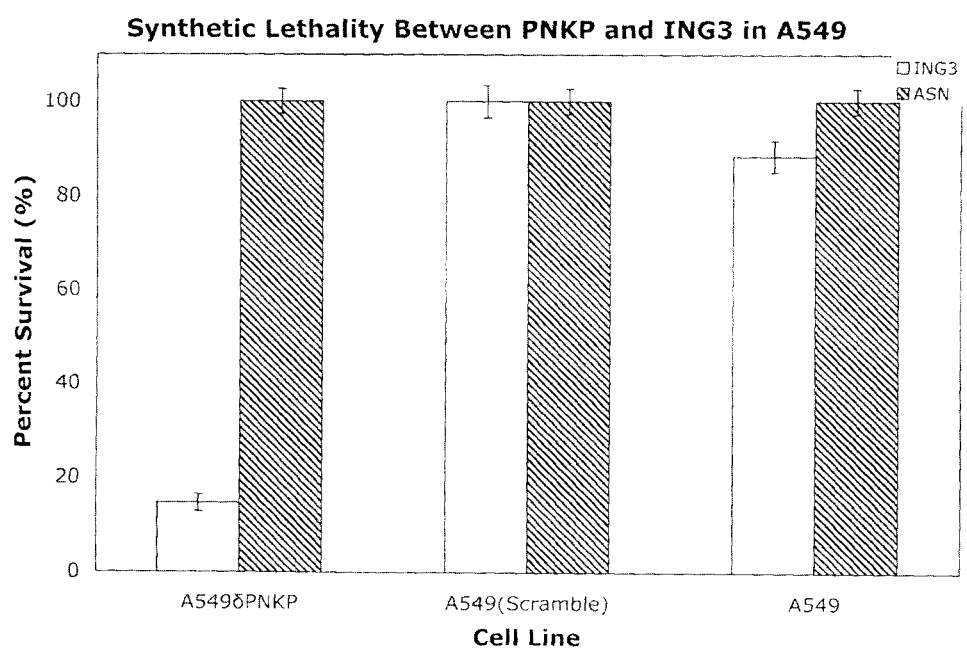
FIG. 4 is a bar graph depicting synthetic lethality between PNKP and ING3 in A549 cells.
Figure 5:
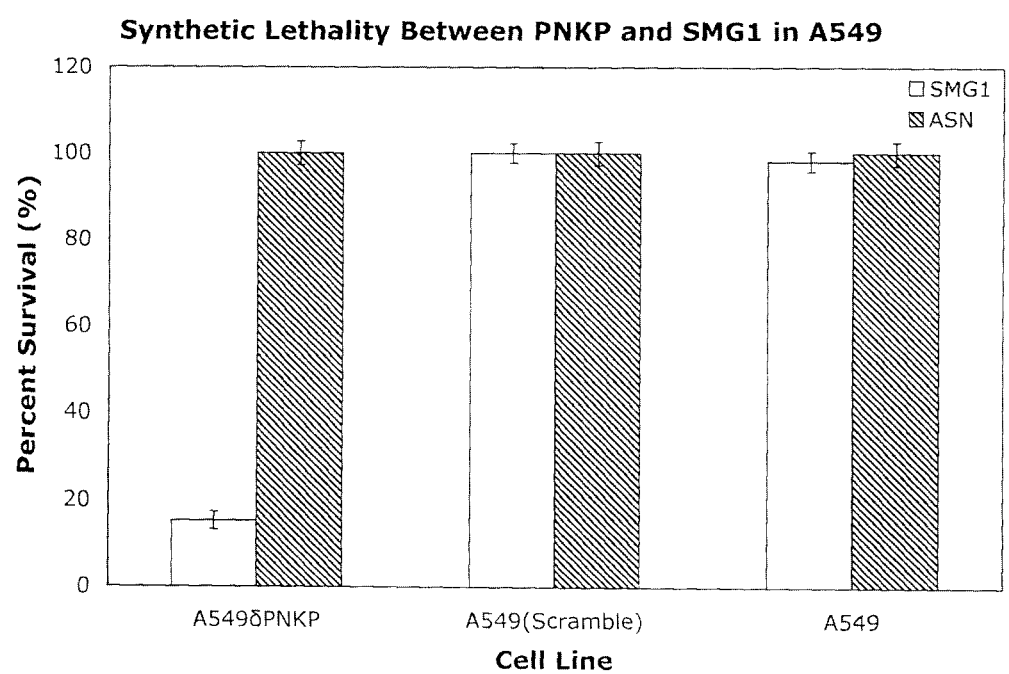
FIG. 5 is a bar graph depicting synthetic lethality between PNKP and SMG1 in A549 cells.
Figure 6:
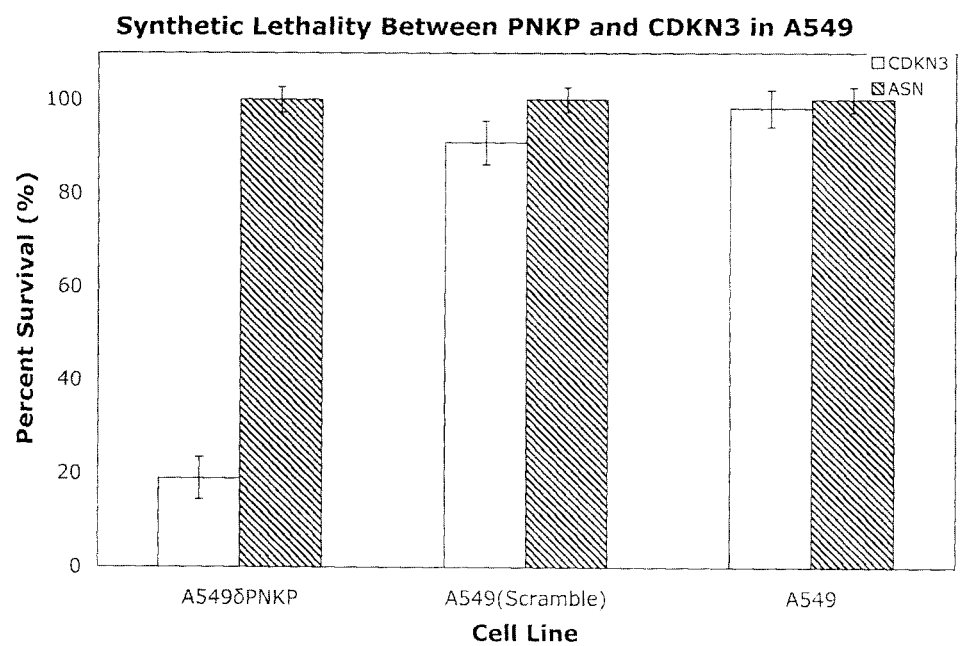
FIG. 6 is a bar graph depicting synthetic lethality between PNKP and CDKN3 in A549 cells.
Figure 7:
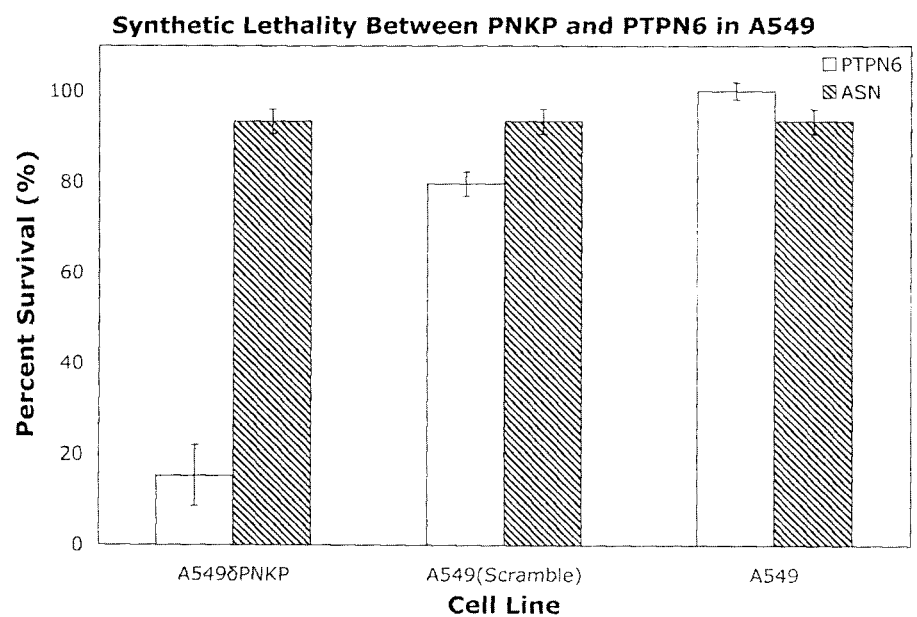
FIG. 7 is a bar graph depicting synthetic lethality between PNKP and PTPN6 in A549 cells.
Figure 8:
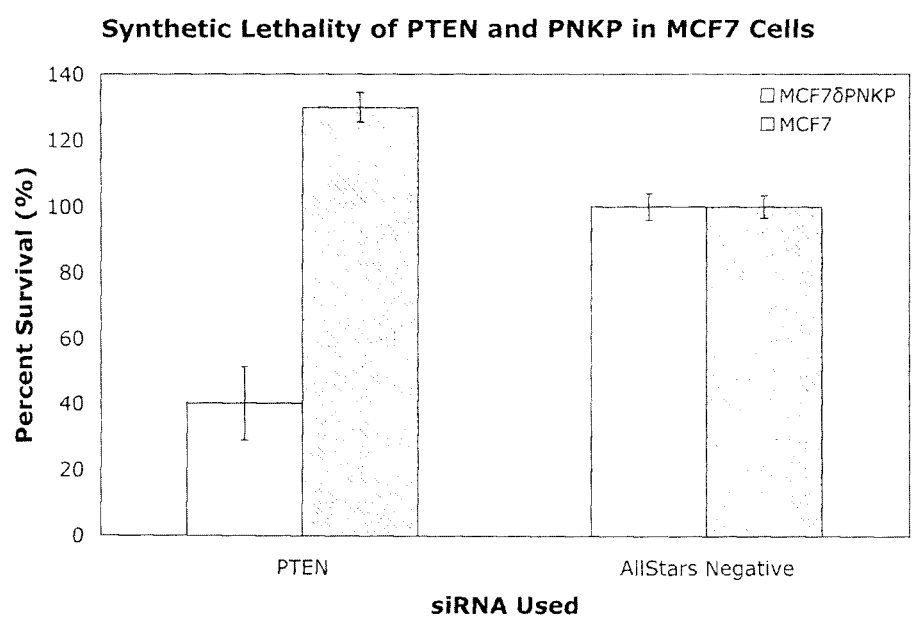
FIG. 8 is a bar graph depicting synthetic lethality of PTEN and PNKP in MCF7.
Figure 9:
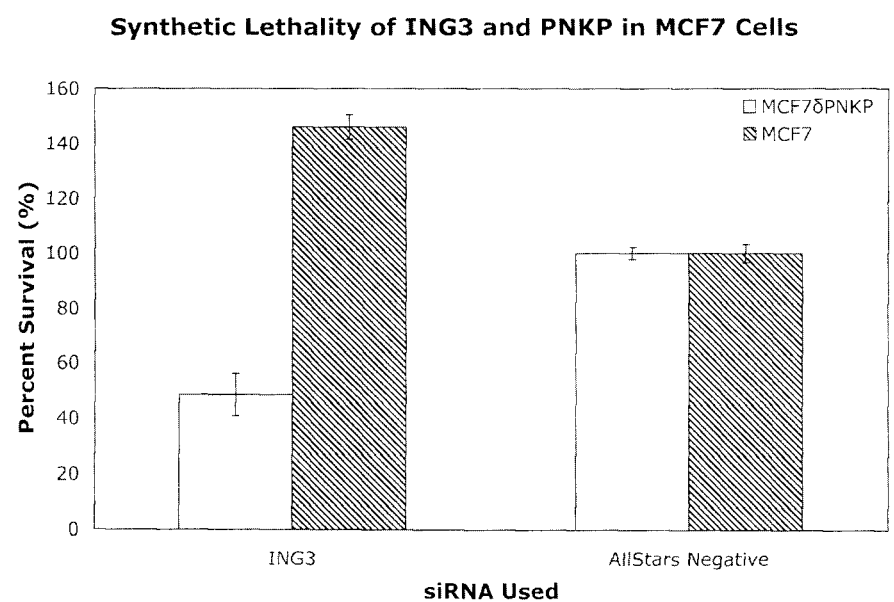
FIG. 9 is a bar graph depicting synthetic lethality of ING3 and PNKP in MCF7 cells.
Figure 10:
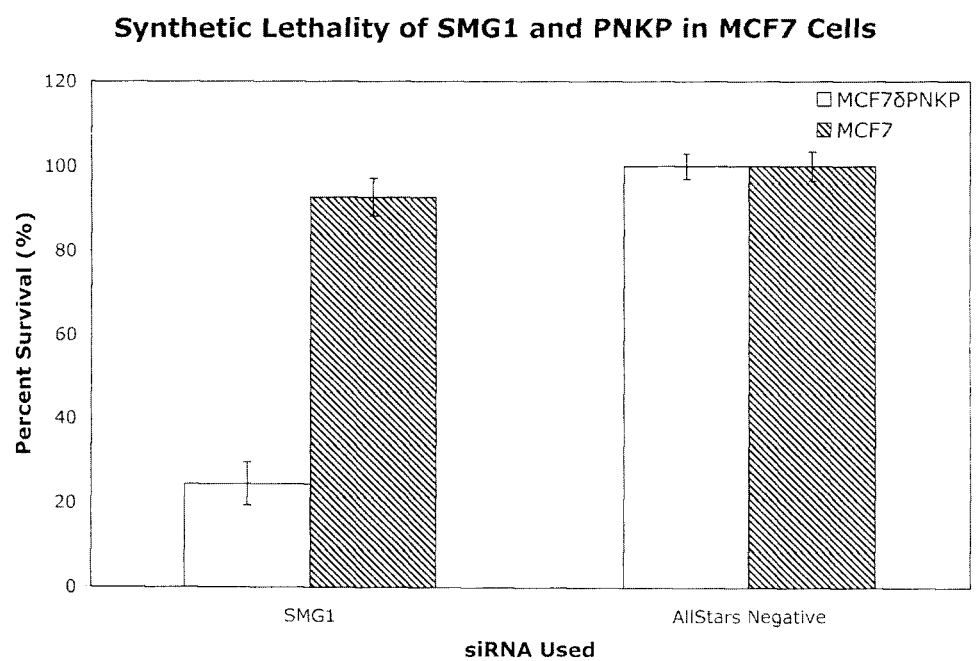
FIG. 10 is a bar graph depicting synthetic lethality of SMG1 and PNKP in MCF7 cells.
Figure 11:
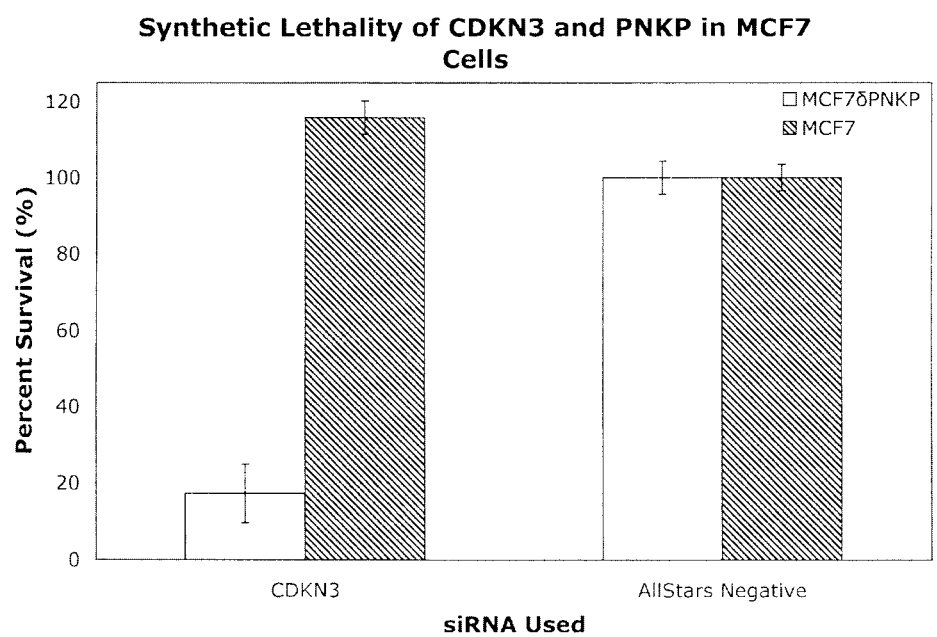
FIG. 11 is a bar graph depicting synthetic lethality of CDKN3 and PNKP in MCF7 cells.

FIG. 2 demonstrates synthetic lethality between PNKP and selected hits from siRNA Screen;

FIGS. 3 to 7 demonstrate synthetic lethality between PNKP and PTEN, ING3, SMG1, CDKN3 and PTPN6, respectively, in A549 cells.

FIGS. 8 to 11 demonstrate synthetic lethality of PTEN, ING3, SMG1 and CDKN3, respectively, with PNKP in MCF7 cells.

Figure 12:
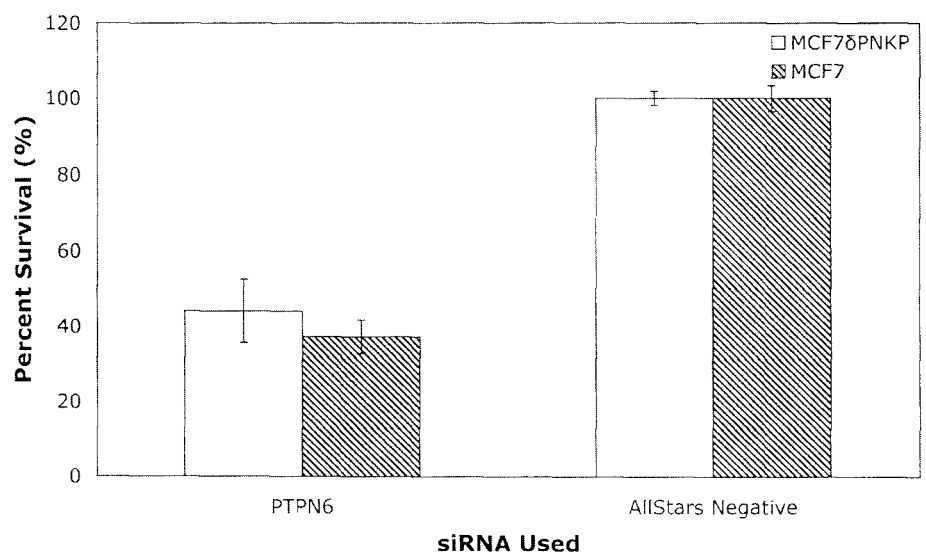
FIG. 12 is a bar graph depicting singular lethality of PTPN6 in MCF7 and MCF7δPNKP cells.
Figure 13:
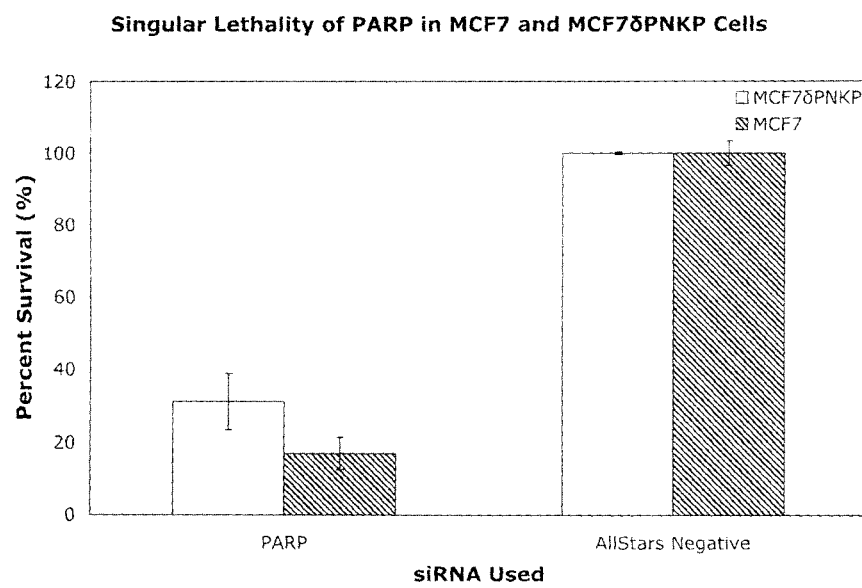
FIG. 13 is a bar graph depicting singular lethality of PARP in MCF7 and MCF7δNKP cells.

FIG. 12 demonstrates singular lethality of PTPN6 in MCF7 and MCF7δPNKP cells;

FIG. 13 demonstrates singular lethality of PARP in MCF7 and MCF7δPNKP cells.

Several tumor suppressors showing synthetically lethal relationships with PNKP were identified. These include the genes: inhibitor of growth family member 3 (ING3), cyclin dependent kinase inhibitor 3 (CDKN3), the tyrosine-protein phosphatase PTPN6, PTEN and SMG1.

These data support a method to directly target cancer cells for death while simultaneously sparing normal tissues. Disruption of PNKP using RNAi or inhibitors will selectively kill cancer cells while sparing normal tissues, thereby reducing the side effects typically associated with cancer treatment. This is because the single disruption of PNKP alone does not harm cells.

Example—II

Materials and Methods

Cells

A549 (human lung carcinoma) and MCF7 (human breast adenocarcinoma) cell lines were obtained from the American Type Culture Collection (Manassas, Va.). The cells were cultured at 37° C. and 5% CO$_2$ in a humidified incubator in a 1:1 mixture of Dulbecco's Modified Eagle's Medium and F12 (DMEM/F12) supplemented with 10% fetal bovine serum (FBS), L-glutamine (2 mM), non-essential amino acids (0.1 mM) and sodium pyruvate (1 mM). All culture supplements were purchased from Invitrogen (Carlsbad, Calif.), and all A549- and MCF7-based cell lines for which transfections were done were cultured under these conditions. For comet assays and apoptosis/necrosis detection penicillin (50 μg/mL) and streptomycin (50 μg/mL) were added to the DMEM/F12 (complete DMEM/F12). All ALCL cell lines were cultured in RPMI-1640 medium (Sigma-Aldrich, Oakville, ON) supplemented with 10% FBS, 0.3 g/L L-glutamine and 2 g/L NaHCO$_3$.

Plasmids

All cell lines were generated by stably transfecting pSUPER.neo vectors (Oligoengine, Seattle, Wash.) into A549 or MCF7 cells yielding several distinct cell lines. AnshRNA directed against nucleotides 1391-1410 of PNKP was used to stably deplete PNKP in A549 and MCF7 cells (A549δPNKP and MCF7δPNKP, respectively) and another shRNA expression vector targeting nucleotides 1313-1333 of SHP-1 was used to generate A549δSHP-1 cells. A control cell line was also generated in which shRNA to no known gene target (a scrambled shRNA) was expressed in A549 cells (A549(Scramble)).

Stable Transfections 20,000 A549 or MCF7 cells were plated and allowed to adhere overnight in a 24-well dish at 37° C. and 5% CO$_2$. 1 μg of pSUPER.neo plasmid DNA was then incubated in 50 μL total of Opti-MEM (Invitrogen) at the same time as 3 μL of Lipofectamine2000 (Invitrogen) was incubated in 50 uL total Opti-MEM at room temperature for 5 minutes. The plasmid DNA solution was then combined with the Lipofectamine2000 solution and incubated at room temperature for 20 minutes. The media from the pre-plated A549 cells was removed and the transfection complexes were added and incubated for 24 h at 37° C. and 5% CO$_2$. The cells were then trypsinized and passaged into 6×100 mm plates in DMEM/F12 without antibiotics and incubated overnight at 37° C. and 5% CO$_2$. The following day, media was removed and replaced with complete DMEM/F12 containing 500 μg/mL G418. After single-clone colonies were formed (10-18 days) the colonies were picked and expanded prior to protein analysis.

Protein Analysis

1×100 mm plate of stably transfected cells was washed twice with ice cold PBS, trypsinized, and spun down at 1500 rpm for 10 minutes at 4° C. The supernatant was aspirated and the cell pellet was then resuspended in 200 μL of CHAPS buffer (0.5% CHAPS, 137 mM NaCl, 50 mM Tris-HCl pH 7.5, and 1 mM EDTA) and rocked for 1 hour at 4° C., after which cell debris was spun down at 14,000 rpm for 20 minutes at 4° C. Determination of whole cell lysate concentration was then conducted using the Bradford Assay.

Western blots were conducted using 50 μg of whole cell lysate. Monoclonal antibody towards PNKP (H101) was used as previously described (28). Monoclonal primary antibodies were incubated 1:1000 in 5% PBSMT overnight at 4° C. Polyclonal primary antibodies were incubated 1:4000 in 5% PBSMT for 1 h at room temperature (Abcam, Cambridge, Mass.). All secondary antibodies were incubated 1:5000 for 45 min. at room temperature.

Transient Transfections 4,000 A549δPNKP, A549(Scramble), MCF7δPNKP or MCF7 cells were plated per well in a 96-well plate, and allowed 24 hours to adhere in a humidified incubator at 37° C. and 5% CO$_2$. All wells surrounding samples were filled with 100 μL ddH$_2$O to control for evaporation effects. For protocol optimization and initial verification of selected hits, 56 nM final concentration of siRNA was added to 50 μL total reaction volume in Opti-MEM (Invitrogen). At the same time as siRNA-Opti-MEM incubation, a 1:25 dilution of Dharmafect Transfection Reagent 1 (Dharmacon, Lafayette, Colo.) in Opti-MEM was allowed to incubate at room temperature for five minutes, for a final concentration of 0.23 µL of transfection reagent per well. The two solutions were then combined and transfection complexes were allowed to form at room temperature for 20 minutes. The media was then removed from the cells and 100 µL of the transfection complexes was added per well and the plate was incubated at 37° C. and 5% $CO_2$ for 72 hours. All siRNAs used here were purchased from Qiagen (Mississauga, ON).

siRNA Library Screen

Qiagen's druggable genome was first pooled into 89 total 96-well plates at a concentration of 1 µM, each well containing four separate siRNAs to the same mRNA target. Also added to the plates were three additional control wells (C12, D12 and E12) of AllStars Negative (ASN) scrambled siRNA (Qiagen). Then, utilizing the JANUS Automated Workstation (PerkinElmer, Waltham, Mass.), 4,000 A549δPNKP or A549(Scramble) cells were seeded in duplicate into each well of a 96-well plate in a final volume of 100 µL DMEM/F12 without penicillin/streptomycin and allowed to adhere overnight in a humidified incubator. The following day, transfection complexes were generated as described above (56 nM siRNA and a total of 0.23 µL Dharmafect transfection reagent 1/well), media was aspirated from the plates containing cells, and 100 µL of the complexes were added to each well and allowed to incubate for 72 hours. After incubation 10% v/v of 440 µM Alamar Blue (Sigma-Aldrich, Oakville, ON) was added to each well and allowed to incubate for 50-90 minutes after which fluorescence was read using the EnVision 2104 Multilabel Reader (PerkinElmer) with a 540 nm excitation filter and a 590 nm emission filter.

Transient transfections for synthetic lethal interactors were used for confirmatory assays, however each siRNA was used separately and at a concentration between 20-40 nM. All other reagent concentrations remained constant. Each assay was done by hand and the samples' fluorescence was read with a FLUOstar Optima® plate reader (BMG Labtec Inc. Durham, N.C.) using a 540 nm excitation filter and a 590 nm emission filter.

Cell Proliferation Assay with ALCL Cell Lines

Karpas 299 or SUPM2 cells were plated in 96-well format at a concentration of 5,000 cells/100 µL in complete RPMI. Increasing concentrations of the PNKP inhibitor A12B4C3 was added to each well at a constant concentration of DMSO and left to incubate for 12-16 days. 11 µL of 440 µM Alamar Blue was then loaded onto the plates and left to incubate for 24-48 hours after which fluorescence was determined as described above.

Single-Cell Gel Electrophoresis

A549(Scramble), A549δPNKP and A549δSHP-1 cells were grown to confluence in 60 mm plates in complete DMEM/F12. The cells were irradiated with 5 Gy ($^{60}$Co Gammacell; Atomic Energy of Canada Limited, Ottawa, Canada) and incubated at 37° C. for 0, 10, 30, 60 or 120 minutes for the alkaline comet assay and 0, 2, 6, and 24 hours for neutral comet assays. Controls were also included in which cells were not irradiated to give the baseline level of DNA damage present in each cell line. Single and double-strand breaks were then determined by single-cell gel electrophoresis as previously described (27).

Mode of Cell Death Determination

A549(Scramble) or A549δPNKP cells were grown on coverslips in complete DMEM/F12 and were either transfected with ASN or SHP-1. Another control subjected these cell lines to 100 µM 5-(p-Bromobenzylidine)-α-isopropyl-4-oxo-2-thioxo-3-thiozolidineacetic acid (BH3I-1, Sigma-Aldrich, Oakville, ON), which is a known apoptosis inducer. The cells were grown under each condition for the indicated length of time before being subjected to a triple stain of Hoescht 33342, Ethidium Homodimer III and Annexin V-FITC (Biotium, Hayward, Calif.). Hoescht 33342 is an uncharged DNA stain that will stain the nuclei of healthy and non-healthy cells alike, however, Ethidium Homodimer III is a highly positively charged DNA stain that cannot readily enter cells unless there is a loss of membrane integrity. In this way, we will be able to identify those cells that are late apoptotic or necrotic by distinguishing those cells that fluoresce due to Ethidium Homodimer III. Early apoptotic cells were identified through the fluorescing of the FITC molecule conjugated to the phosphatidylserine-detecting Annexin V protein.

Results—II siRNA Screen for the Synthetic Lethal Partners of PNKP

The screen was performed in duplicate using A549δPNKP and A549(Scramble) cells under identical conditions (c.f. FIG. 1) and survival was compared to controls. Cells were exposed to transfection complexes continuously for 72 hours allowing for at least two cell cycles to occur at a concentration known to be effective at knocking down target proteins. Cell survival was then determined by an Alamar Blue-based reduction assay (30).

Figure 16:
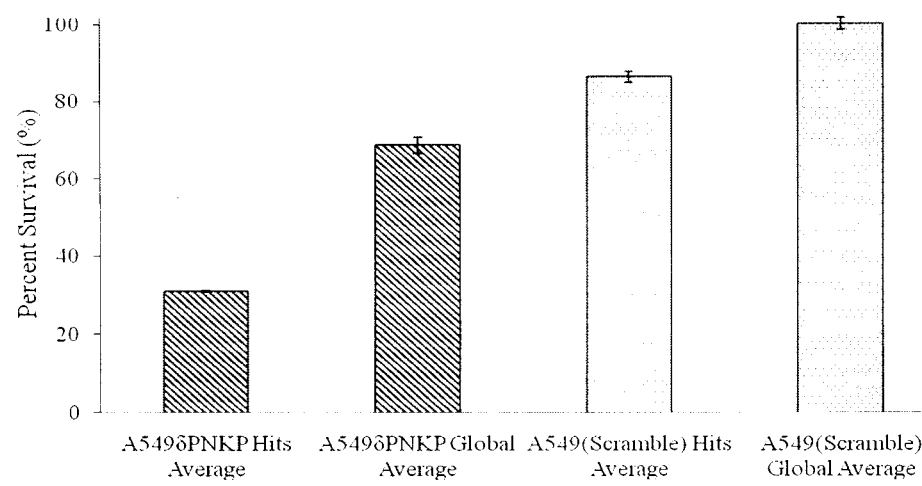
FIG. 16 depicts the averages for A549δPNKP (hatched bars) and A549(Scramble) (speckled bars) siRNA library screens.

When the duplicate screens were compared to each another, they were shown to be highly reproducible and the total averages are outlined in FIG. 16. Cell survival scores of each siRNA were compared to controls located on the same plate, and a master list of potential synthetic lethal partners was generated. We then examined the list for hits, which were designated as a survival of <30% compared to controls. The hit rate was found to be 6.9% (478/6961) including 32 phosphatases, 97 kinases, 117 G-protein coupled receptors and 232 unclassified proteins. 17 tumor suppressors were identified as potentially synthetic lethal with PNKP, including the protein tyrosine phosphatase SHP-1.

Identification of SHP-1 as a Possible Synthetic Lethal Partner of PNKP

A balance of protein tyrosine phosphorylation exists in the cell and is regulated by protein tyrosine kinases and phosphatases. They are responsible for the regulation of cell proliferation, metabolism, differentiation, migration, adhesion and cell communication (31, 32). One hit for synthetic lethality with PNKP identified in the screen is SHP-1. SHP-1 is a protein tyrosine phosphatase that has been implicated as a tumor suppressor, functioning in the regulation of signal transduction pathways (31) and opposes growth-promoting and oncogenic signals through its phosphatase activity (33).

We used siRNA to transiently knockdown SHP-1 in various cell lines, utilizing multiple distinct siRNAs to the same gene target both independently and pooled, the lowest possible siRNA concentration, rational design filters and finally a different method of protein disruption using small chemical inhibitors. We reduced the concentration of siRNA used in the screen by up to 3.5× and repeated the assay using each of the four pooled siRNAs separately.

Figure 17A:
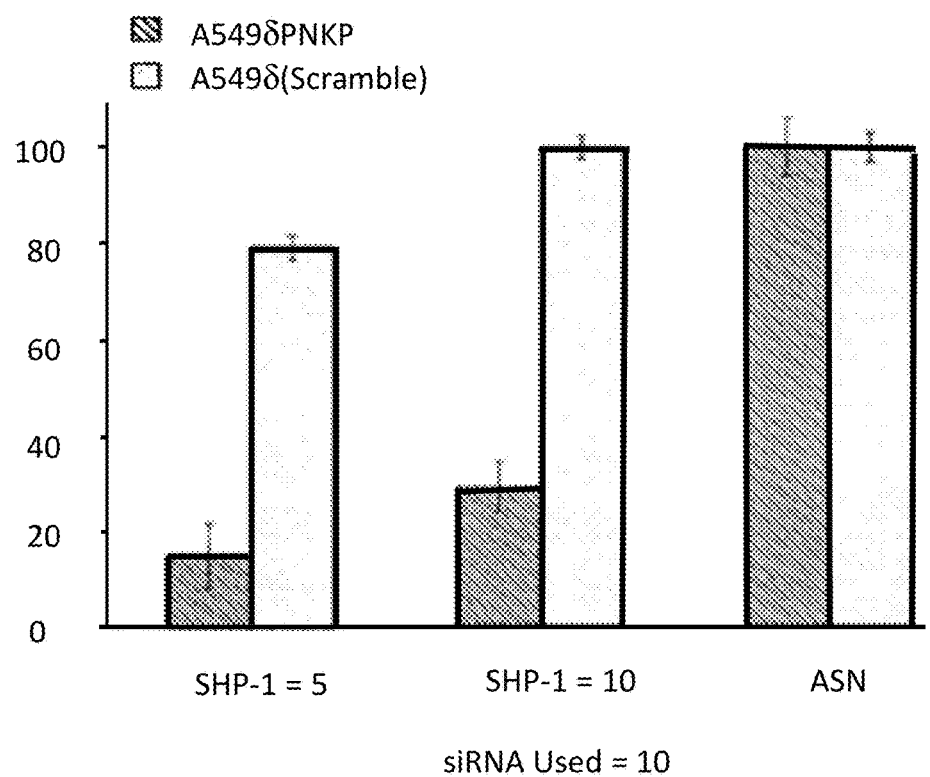
FIGS. 17A and 17B depict confirmation of synthetic lethality between SHP-1 and PNKP. ASN=AllStars Negative (Qiagen) scrambled control siRNA.

When four distinct siRNAs directed toward SHP-1 were assayed, all four displayed selective killing of A549δPNKP cells and no toxicity in control cells (FIG. 17A, only top two siRNAs shown, #5 Z-factor=~12.3, p<0.001; #10 Z-factor=−17.2, p<0.001). Therefore, targeting PNKP function for disruption may provide substantial benefit for those whose cancers lack SHP-1. According to the Oka et al. a high percentage of leukemias and lymphomas lack SHP-1 (35). Specifically, when 207 paraffin embedded tumor biopsies were assayed, 40/45 malignant prostate tissues, 95% of various malignant lymphomas and 100% of NK and T cell lymphomas showed diminished or absent SHP-1 expression (35).

Confirmation of Synthetic Lethal Partnerships in MCF7 Cells

We performed the cell proliferation assay using 20 nM of SHP-1 siRNA using both a stable knockdown of PNKP in MCF7 (MCF7δPNKP) and the MCF7 parental cell line.

Figure 17B:
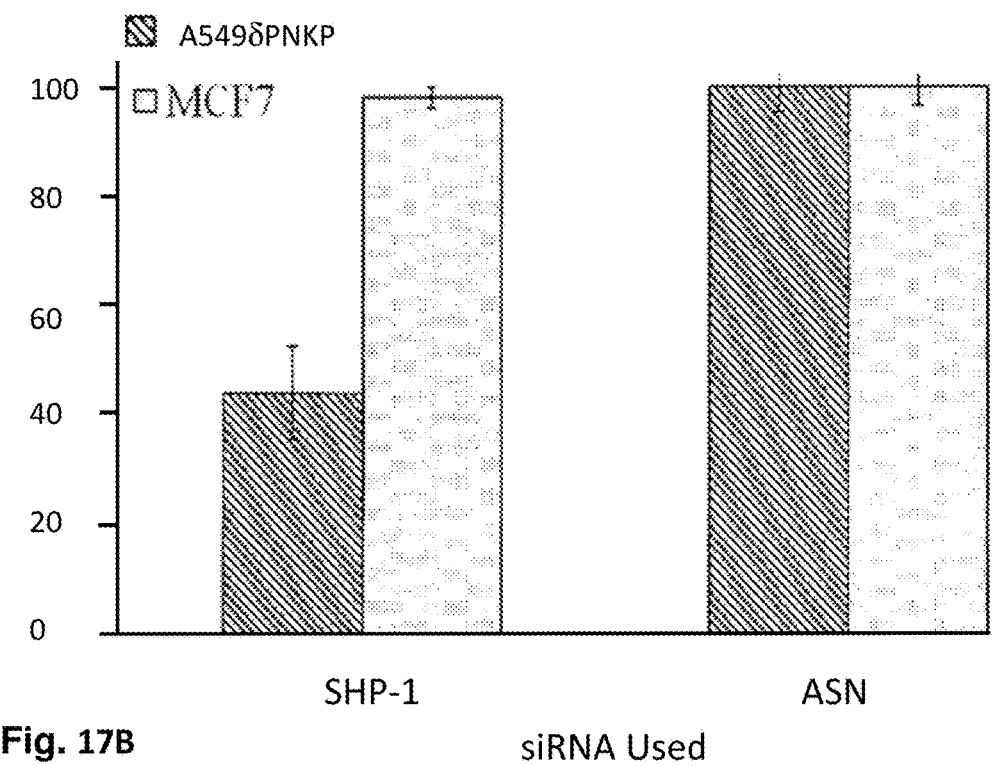
Figure 18:
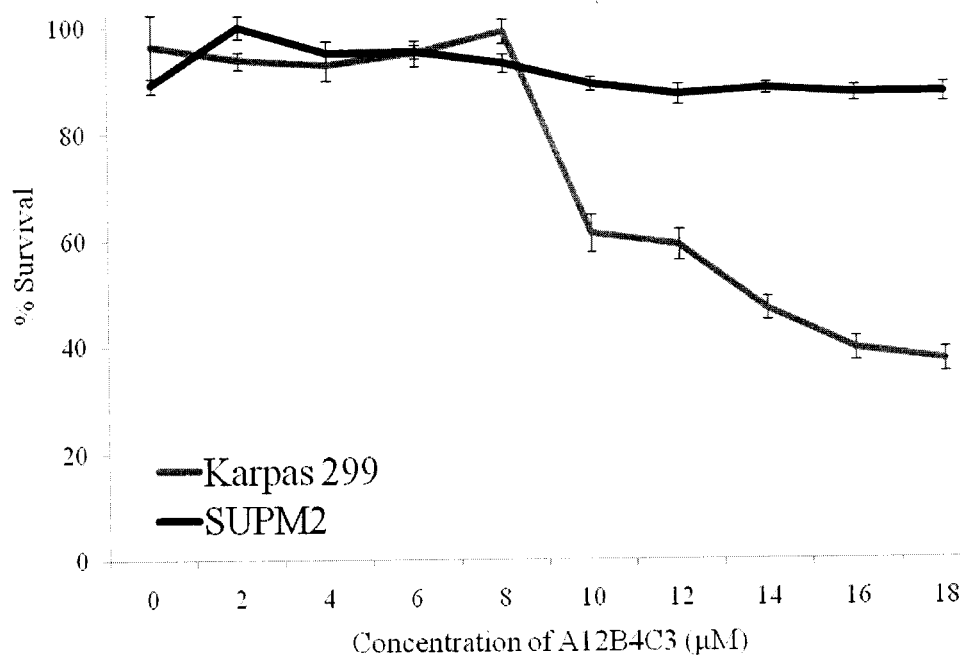
FIG. 18 depicts survival of Karpas 299 cells under PNKP inhibition. Karpas 299 (ALCL cells naturally depleted of SHP-1$^{-/-}$) were treated with an increasing concentration of the PNKP inhibitor A12B4C3 alongside a control ALCL cell line SUPM2, which contains normal levels of SHP-1.

The assay was again performed over 72 consecutive hours after which Alamar Blue was added at 10% v/v and left for 50-120 minutes. As is seen in A549 cells, the double disruption of both SHP-1 and PNKP is responsible for lethality and each individual knockdown is not lethal (FIG. 17B, Z-score=−3.4, p<0.001), nor is the activation of RNAi machinery responsible for lethality. These results indicate this effect is present across a range of cancer subtypes and that it may be possible to take advantage of this association to treat many different cancers.

Survival of Naturally Occurring SHP-1 Positive and Negative Cells to PNKP Inhibition Using A12B4C3

Karpas 299 (naturally SHP-1$^{-/-}$) and SUPM2 (naturally SHP-1$^{+/+}$) cells were subjected to an increasing concentration of the PNKP inhibitor A12B4C3 over a period of 12-16 days (26). At approximately 10 μM of A12B4C3 there is a marked decrease in survival of the SHP-1$^{-/-}$ cells yet the SHP-1$^{+/+}$ cells remain viable. This indicates the utility of exploiting the synthetic lethal relationship between PNKP and SHP-1.

Single-Cell Gel Electrophoresis (Comet Assay)

Figure 19A:
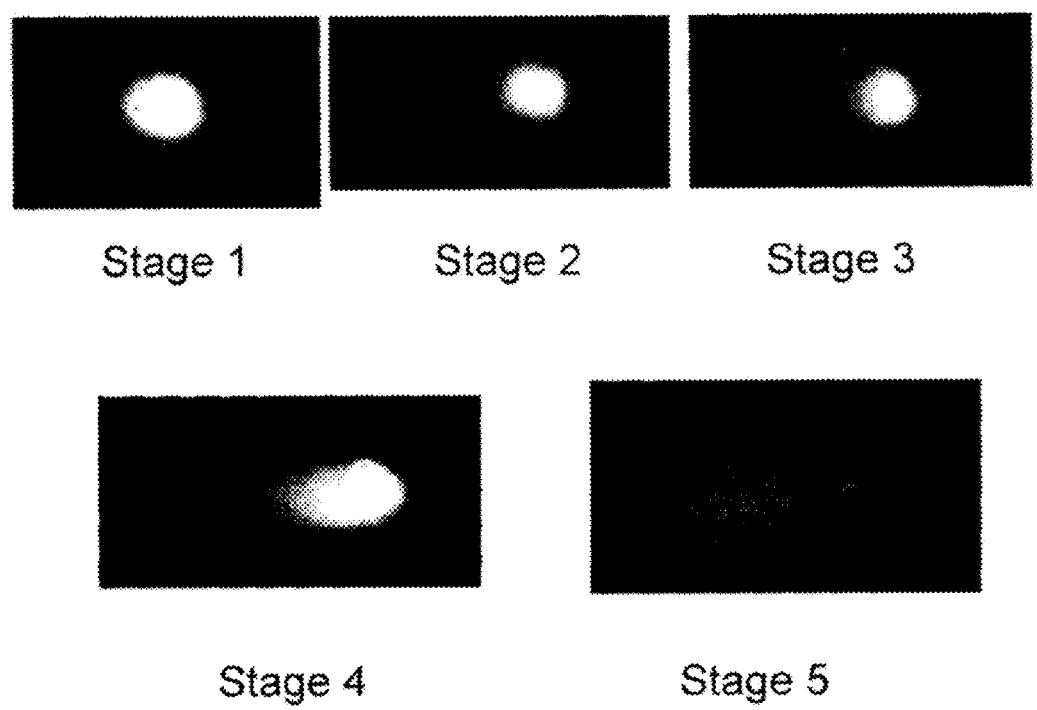
FIGS. 19A-19D depict incidence of SSBs using alkaline single-cell gel electrophoresis (comet assay). Cells were plated 24 h in advance after which they were subjected to 5 Gy of γ-radiation. The cells were then allowed specific time periods for DNA repair to occur before being electrophoresed.
Figure 19B:
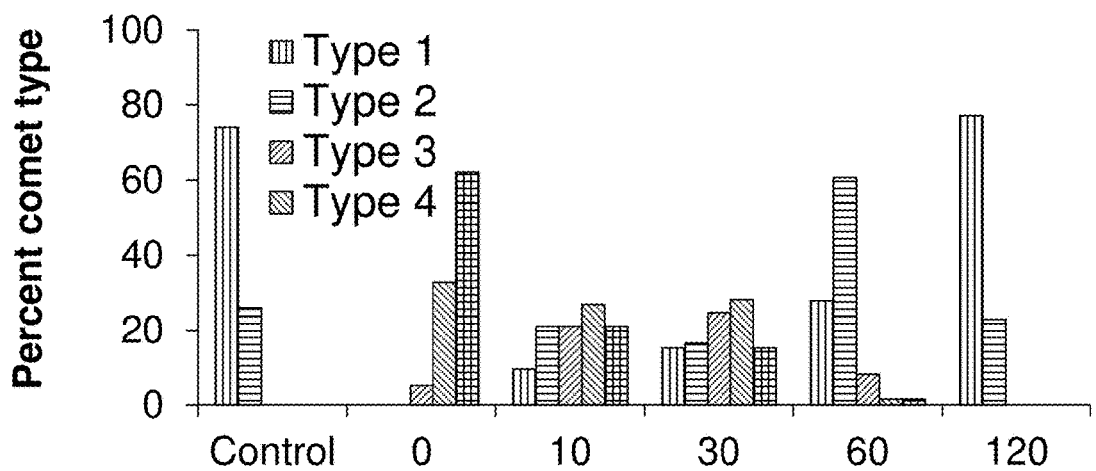
Figure 19C:
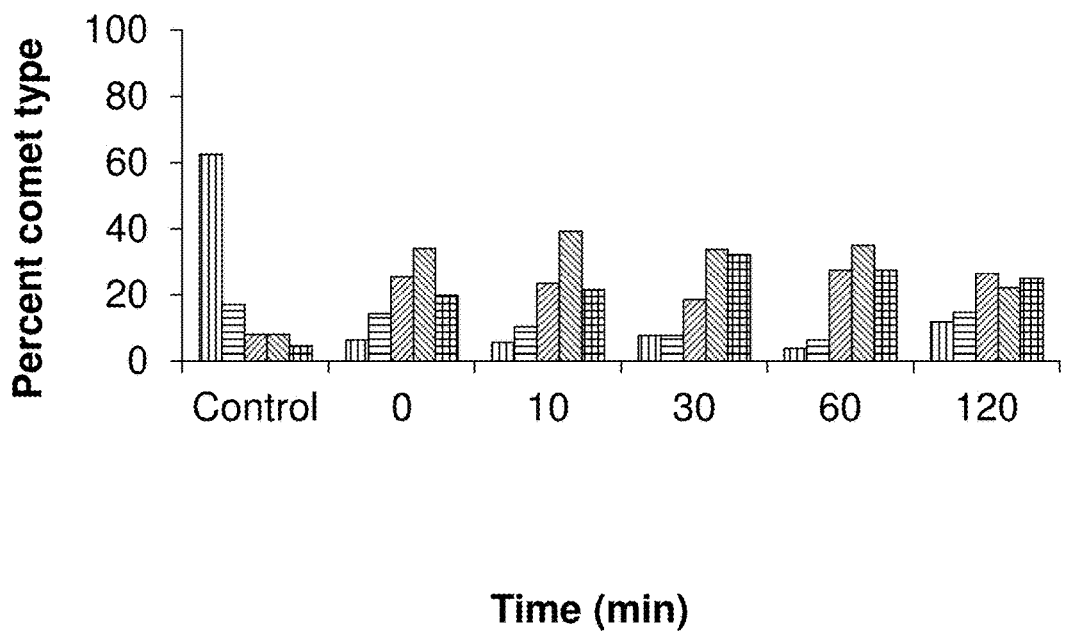
Figure 19D:
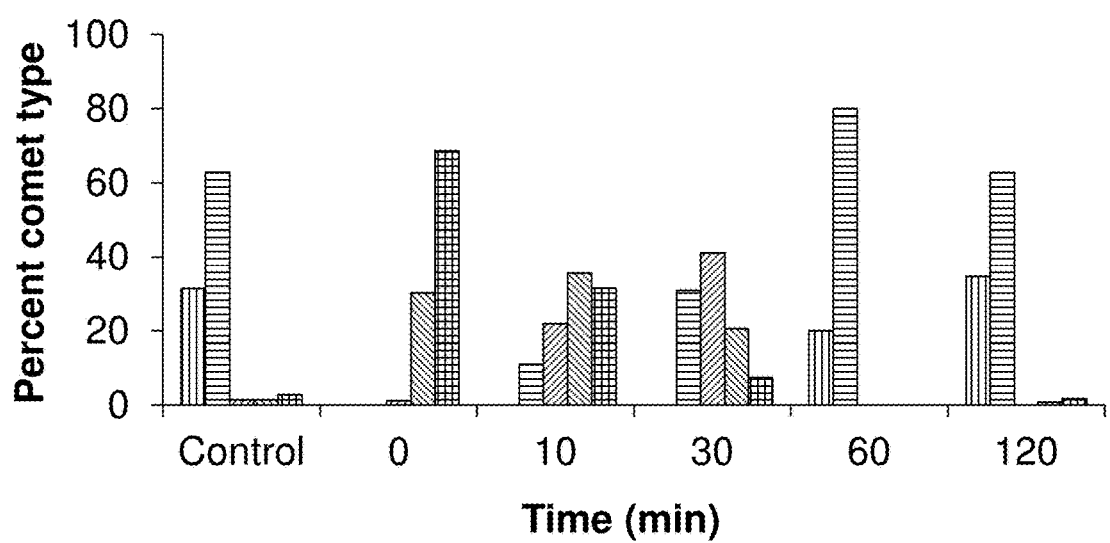

SHP-1 is known to negatively regulate receptor tyrosine kinase (RTK) signaling, and unchecked RTK signaling through deregulation of SHP-1 is critical for the development or progression of several cancers (31, 39). SHP-1, however, is not established as a DNA repair protein. We performed alkaline and neutral comet assays (typical comets are seen in FIG. 19A). When A549(Scramble) cells are subjected to the alkaline comet assay, there is total repair back to baseline levels of damage after 120 minutes (FIG. 19B). However, when A549δPNKP (a known DNA repair protein) cells undergo the same treatment, there appears to be a slight retardation of repair, shown by the presence of higher stage comets at 120 minutes which are not present in control cells (FIG. 19C). When SHP-1 knockdown cells are subjected to the alkaline comet assay, there is no delay of repair, however, there is a noticeable increase in the amount of damage present in untreated cells as evidenced by a large proportion of cells showing stage 2 comets or above (FIG. 19C). While not wishing to be bound by theory, since repair is completed to baseline levels after 120 minutes, SHP-1 does not seem to be directly involved in the repair of SSBs.

Figure 20C:
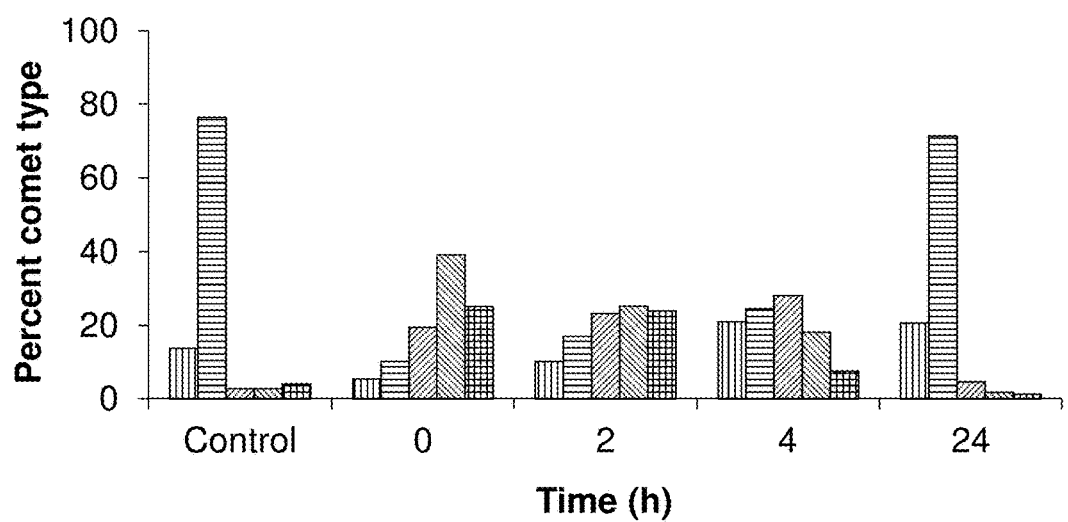

When the same cells are subjected to the neutral comet assay to check for DSBR, most repair is completed in A549(Scramble) by 24 hours, however, there is a severe retardation of repair in A549δPNKP cells (FIGS. 20A and 20B, respectively). However, as with SSBR, the repair of DSBs in A549δSHP-1 cells is completed within 24 hours as is seen in control cells indicating that SHP-1 is not involved in DSBR (FIG. 20C).

Mechanism of Cell Death

The mode of synthetic lethality-induced cell death is of interest. Cells undergoing necrosis lose membrane integrity early and release cytotoxic constituents that can damage neighboring cells, or induce an undesirable immune response (46). However, apoptotic cells do not cause such an immune response. They are recognized by the host immune system and phagocytized by macrophages in highly regulated process that tissue homeostasis and immune regulation depends on (46).

Figure 21A:
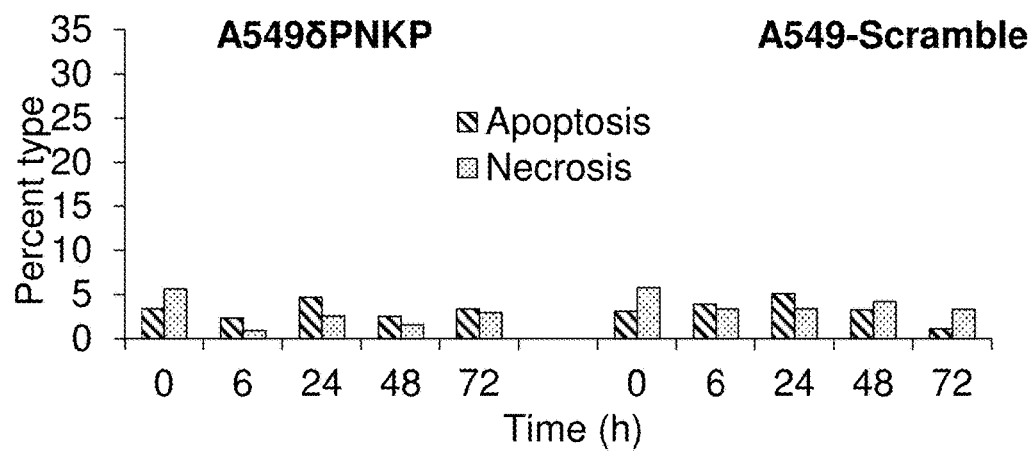
FIGS. 21A-21C depict mode of death of cells undergoing synthetic lethality due to the simultaneous disruption of SHP-1 and PNKP.
Figure 21B:
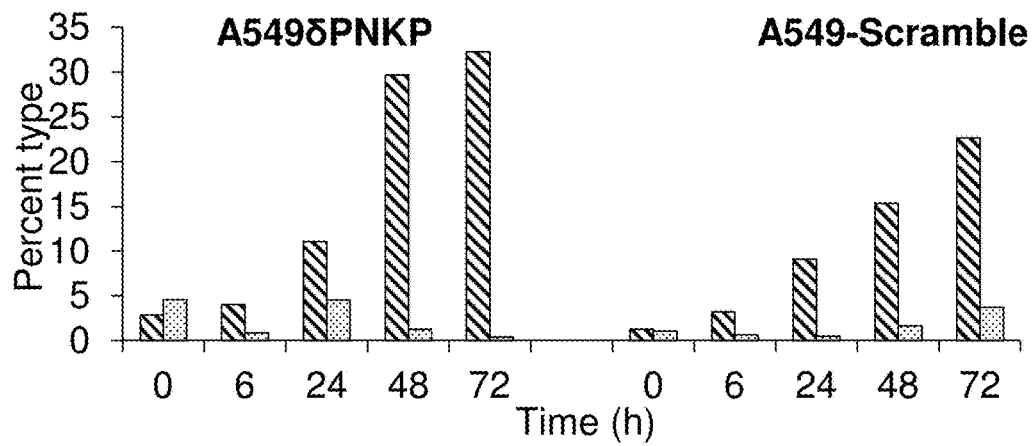
Figure 21C:
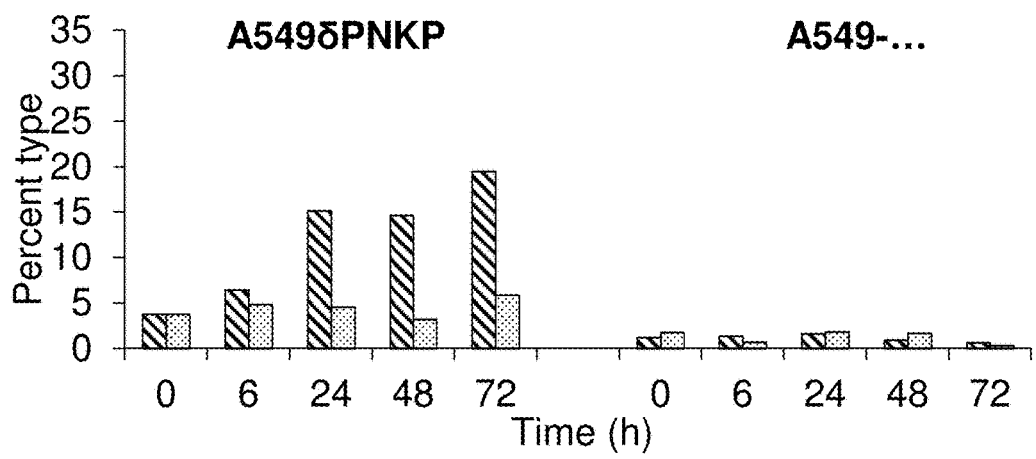

To identify the mechanism in which cells undergo synthetic lethality upon simultaneous disruption of SHP-1 and PNKP, A549(Scramble) and A549δPNKP cells were grown on coverslips and transiently transfected with ASN or SHP-1 siRNA (FIGS. 21A and 21C, respectively). As a control, cells were treated with the apoptosis inducer BH3I-1 (FIG. 21B). Cells were then simultaneously stained with Hoescht 33342, EthidiumHomodimer III and Annexin V-FITC, which fluoresce at different wavelengths (absorbance/emission; 350/461 nm, 528/617 nm, and 492/514 nm, respectively). Hoescht 33342 is an uncharged DNA stain that will stain the nuclei of healthy and non-healthy cells alike, however, EthidiumHomodimer III is a highly positively charged DNA stain that cannot readily cross cell membranes unless there is a loss of membrane integrity. In this way, those cells that are late apoptotic or necrotic are identified by distinguishing those cells that fluoresce due to EthidiumHomodimer III. Early apoptotic cells were identified through the fluorescing of the FITC molecule conjugated to the phosphatidylserine-detecting Annexin V protein.

FIG. 21A shows there is a small percentage of cells that are both apoptotic and necrotic upon transfection of both cell lines with ASN. Upon treatment of these cell lines with BH3I-1, there is a substantial increase in the occurrence of apoptotic cells (FIG. 21B). When cells contain a double knockdown of SHP-1 and PNKP, there is a similar increase in the number of apoptotic cells present indicating that cells undergoing SHP-1/PNKP induced synthetic lethality are apoptotic (FIG. 21C).

Discussion—II

Our screen identified synthetic lethal interactors of PNKP, which are either known as or are implicated as tumor suppressors. Cancers lacking any of these tumor suppressors may be selectively sensitive to targeted PNKP disruption. SHP-1, for example, has been shown to be deficient or absent in a substantial number of human cancers (31, 35, 39).

SHP-1 is protein product of the protein tyrosine phosphatase, non-receptor type 6 (PTPN6) gene and is part of the protein tyrosine phosphatase (PTP) family. PTPs play an important role in regulation of signaling pathways often disturbed in cancer cells (50) and SHP-1 dysfunction, specifically, has been noted to induce lymphomas and leukemias and often shows reduced expression in these, and other cancers (50, 51). When cDNA expression array and tissue microarray techniques were performed to assay SHP-1 status of 207 paraffin-embedded samples of various cancers, the results were staggering. 89% of malignant prostate tissues, 95% of various malignant lymphomas and 100% of NK and T cell lymphomas showed no detectable SHP-1 expression (35, 50, 51).

The synthetic lethal relationship between PNKP and SHP-1 is evident in genotypically distinct cancer types and undergo apoptosis when doubly disrupted.

While not wishing to be bound by theory, SHP-1 is also not directly involved in DNA repair, suggesting an alternative mechanism for synthetic lethality beyond widely accepted models (4, 6, 37, 42). Also while not wishing to be bound by theory, we have shown that SHP-1 depletion in A549 and MCF7 cells also causes an increase in ROS production, which when coupled with PNKP-mediated disruption of DNA repair causes a cytotoxic accumulation of DNA damage.

REFERENCES

1. Dobzhansky T. Genetics of Natural Populations. Xiii. Recombination and Variability in Populations of *Drosophila Pseudoobscura*. Genetics 1946; 31(3):269-90.
2. Iglehart J D, Silver D P. Synthetic lethality—a new direction in cancer-drug development. N Engl J Med 2009; 361(2):189-91.
3. Lucchesi J C. Synthetic lethality and semi-lethality among functionally related mutants of *Drosophila melanfgaster*. Genetics 1968; 59(1):37-44.
4. Bryant H E, Schultz N, Thomas H D, Parker K M, Flower D, Lopez E, et al. Specific killing of BRCA2-deficient tumours with inhibitors of poly(ADP-ribose) polymerase. Nature 2005; 434(7035):913-7.
5. Comen E A, Robson M. Poly(ADP-ribose) polymerase inhibitors in triple-negative breast cancer. Cancer J 2010; 16(1):48-52.
6. Farmer H, McCabe N, Lord C J, Tutt A N, Johnson D A, Richardson T B, et al. Targeting the DNA repair defect in BRCA mutant cells as a therapeutic strategy. Nature 2005; 434(7035):917-21.
7. Fong P C, Boss D S, Yap T A, Tutt A, Wu P, Mergui-Roelvink M, et al. Inhibition of poly(ADP-ribose) polymerase in tumors from BRCA mutation carriers. N Engl J Med 2009; 361(2):123-34.
8. Bolderson E, Richard D J, Zhou B B, Khanna K K. Recent advances in cancer therapy targeting proteins involved in DNA double-strand break repair. Clin Cancer Res 2009; 15(20):6314-20.
9. O'Connor M J, Martin N M, Smith G C. Targeted cancer therapies based on the inhibition of DNA strand break repair. Oncogene 2007; 26(56):7816-24.
10. Amir E, Seruga B, Serrano R, Ocana A. Targeting DNA repair in breast cancer: a clinical and translational update. Cancer Treat Rev 2010; 36(7):557-65.
11. BiPar Sciences presents interim phase 2 results for PARP inhibitor BSI-201 at San Antonio Breast Cancer Symposium. Cancer Biol Ther 2009; 8(1):2-3.
12. Pal S K, Mortimer J. Triple-negative breast cancer: novel therapies and new directions. Maturitas 2009; 63(4):269-74.
13. Dungey F A, Caldecott K W, Chalmers A J. Enhanced radiosensitization of human glioma cells by combining inhibition of poly(ADP-ribose) polymerase with inhibition of heat shock protein 90. Mol Cancer Ther 2009; 8(8):2243-54.
14. Evers B, Schut E, van der Burg E, Braumuller T M, Egan D A, Holstege H, et al. A high-throughput pharmaceutical screen identifies compounds with specific toxicity against BRCA2-deficient tumors. Clin Cancer Res 2010; 16(1): 99-108.
15. O'Brien T, Stokoe D. Converting cancer mutations into therapeutic opportunities. EMBO Mol Med 2009; 1(6-7): 297-9.
16. Stefansson O A, Jonasson J G, Johannsson O T, Olafsdottir K, Steinarsdottir M, Valgeirsdottir S, et al. Genomic profiling of breast tumours in relation to BRCA abnormalities and phenotypes. Breast Cancer Res 2009; 11(4):R47.
17. Venkitaraman A R. Targeting the molecular defect in BRCA-deficient tumors for cancer therapy. Cancer Cell 2009; 16(2):89-90.
18. Williamson C T, Muzik H, Turhan A G, Zamo A, O'Connor M J, Bebb D G, et al. ATM deficiency sensitizes mantle cell lymphoma cells to poly(ADP-ribose) polymerase-1 inhibitors. Mol Cancer Ther; 9(2):347-57.
19. Zander S A, Kersbergen A, van der Burg E, de Water N, van Tellingen O, Gunnarsdottir S, et al. Sensitivity and acquired resistance of BRCA1; p53-deficient mouse mammary tumors to the topoisomerase I inhibitor topotecan. Cancer Res; 70(4): 1700-10.
20. Turner N, Tutt A, Ashworth A. Hallmarks of 'BRCAness' in sporadic cancers. Nat Rev Cancer 2004; 4(10): 814-9.
21. Mendes-Pereira A M, Martin S A, Brough R, McCarthy A, Taylor J R, Kim J S, et al. Synthetic lethal targeting of PTEN mutant cells with PARP inhibitors. EMBO Mol Med 2009; 1(6-7):315-22.
22. Lindahl T, Nyberg B. Rate of depurination of native deoxyribonucleic acid. Biochemistry 1972; 11(19):3610-8.
23. Rasouli-Nia A, Karimi-Busheri F, Weinfeld M. Stable down-regulation of human polynucleotide kinase enhances spontaneous mutation frequency and sensitizes cells to genotoxic agents. Proc Natl Acad Sci USA 2004; 101(18):6905-10.
24. Weinfeld M, Mani R S, Abdou I, Aceytuno R D, Glover J N. Tidying up loose ends: the role of polynucleotide kinase/phosphatase in DNA strand break repair. Trends Biochem Sci 2011.
25. Urruticoechea A, Alemany R, Balart J, Villanueva A, Vinals F, Capella G. Recent advances in cancer therapy: an overview. Curr Pharm Des 2010; 16(1):3-10.
26. Freschauf G K, Karimi-Busheri F, Ulaczyk-Lesanko A, Mereniuk T R, Ahrens A, Koshy J M, et al. Identification of a small molecule inhibitor of the human DNA repair enzyme polynucleotide kinase/phosphatase. Cancer Res 2009; 69(19):7739-46.
27. Freschauf G K, Mani R S, Mereniuk T R, Fanta M, Virgen C A, Dianov G L, et al. Mechanism of action of an imidopiperidine inhibitor of human polynucleotide kinase/phosphatase. J Biol Chem 2010; 285(4):2351-60.
28. Fanta M, Zhang H, Bernstein N, Glover M, Karimi-Busheri F, Weinfeld M. Production, characterization, and epitope mapping of monoclonal antibodies against human polydeoxyribonucleotide kinase. Hybridoma 2001; 20(4): 237-42.
29. Bryant H E, Helleday T. Inhibition of poly (ADP-ribose) polymerase activates ATM which is required for subsequent homologous recombination repair. Nucleic Acids Res 2006; 34(6):1685-91.
30. Schindler A, Foley E. A functional RNAi screen identifies hexokinase 1 as a modifier of type II apoptosis. Cell Signal 2010; 22(9):1330-40.
31. Irandoust M, van den Berg T K, Kaspers G J, Cloos J. Role of tyrosine phosphatase inhibitors in cancer treatment with emphasis on SH2 domain-containing tyrosine phosphatases (SHPs). Anticancer Agents Med Chem 2009; 9(2):212-20.
32. Hunter T. The role of tyrosine phosphorylation in cell growth and disease. Harvey Lect 1998; 94:81-119.
33. Wu C, Sun M, Liu L, Zhou G W. The function of the protein tyrosine phosphatase SHP-1 in cancer. Gene 2003; 306:1-12.

34. Turner N C, Lord C J, Iorns E, Brough R, Swift S, Elliott R, et al. A synthetic lethal siRNA screen identifying genes mediating sensitivity to a PARP inhibitor. EMBO J 2008; 27(9):1368-77.
35. Oka T, Yoshino T, Hayashi K, Ohara N, Nakanishi T, Yamaai Y, et al. Reduction of hematopoietic cell-specific tyrosine phosphatase SHP-1 gene expression in natural killer cell lymphoma and various types of lymphomas/leukemias: combination analysis with cDNA expression array and tissue microarray. Am J Pathol 2001; 159(4): 1495-505.
36. Dedes K J, Wilkerson P M, Wetterskog D, Weigelt B, Ashworth A, Reis-Filho J S. Synthetic lethality of PARP inhibition in cancers lacking BRCA1 and BRCA2 mutations. Cell Cycle 2011; 10(8):1192-9.
37. Helleday T. The underlying mechanism for the PARP and BRCA synthetic lethality: Clearing up the misunderstandings. Mol Oncol 2011; 5(4):387-93.
38. Strumberg D, Pilon A A, Smith M, Hickey R, Malkas L, Pommier Y. Conversion of topoisomerase I cleavage complexes on the leading strand of ribosomal DNA into 5'-phosphorylated DNA double-strand breaks by replication runoff Mol Cell Biol 2000; 20(11):3977-87.
39. Kharitonenkov A, Chen Z, Sures I, Wang H, Schilling J, Ullrich A. A family of proteins that inhibit signalling through tyrosine kinase receptors. Nature 1997; 386 (6621):181-6.
40. Gartner E M, Burger A M, Lorusso P M. Poly(adp-ribose) polymerase inhibitors: a novel drug class with a promising future. Cancer J 2010; 16(2):83-90.
41. Gien L T, Mackay H J. The Emerging Role of PARP Inhibitors in the Treatment of Epithelial Ovarian Cancer. J Oncol 2010; 2010:151750.
42. Liang Y, Lin S Y, Brunicardi F C, Goss J, Li K. DNA damage response pathways in tumor suppression and cancer treatment. World J Surg 2009; 33(4):661-6.
43. Lord C J, McDonald S, Swift S, Turner N C, Ashworth A. A high-throughput RNA interference screen for DNA repair determinants of PARP inhibitor sensitivity. DNA Repair (Amst) 2008; 7(12):2010-9.
44. Mizuarai S, Kotani H. Synthetic lethal interactions for the development of cancer therapeutics: biological and methodological advancements. Hum Genet; 128(6):567-75.
45. Underhill C, Toulmonde M, Bonnefoi H. A review of PARP inhibitors: from bench to bedside. Ann Oncol 2010.
46. Krysko D V, D'Herde K, Vandenabeele P. Clearance of apoptotic and necrotic cells and its immunological consequences. Apoptosis 2006; 11(10): 1709-26.
47. Baehrecke E H. How death shapes life during development. Nat Rev Mol Cell Biol 2002; 3(10):779-87.
48. deBakker C D, Haney L B, Kinchen J M, Grimsley C, Lu M, Klingele D, et al. Phagocytosis of apoptotic cells is regulated by a UNC-73/TRIO-MIG-2/RhoG signaling module and armadillo repeats of CED-12/ELMO. Curr Biol 2004; 14(24):2208-16.
49. Canaani D. Methodological approaches in application of synthetic lethality screening towards anticancer therapy. Br J Cancer 2009; 100(8):1213-8.
50. Cariaga-Martinez A E, Lorenzati M A, Riera M A, Cubilla M A, De La Rossa A, Giorgio E M, et al. Tumoral prostate shows different expression pattern of somatostatin receptor 2 (SSTR2) and phosphotyrosine phosphatase SHP-1 (PTPN6) according to tumor progression. Adv Urol 2009:723831.
51. Delibrias C C, Floettmann J E, Rowe M, Fearon D T. Downregulated expression of SHP-1 in Burkitt lymphomas and germinal center B lymphocytes. J Exp Med 1997; 186(9):1575-83.
52. Krotz F, Engelbrecht B, Buerkle M A, Bassermann F, Bridell H, Gloe T, et al. The tyrosine phosphatase, SHP-1, is a negative regulator of endothelial superoxide formation. J Am Coll Cardiol 2005; 45(10):1700-6.
53. Pan X, Ye P, Yuan D S, Wang X, Bader J S, Boeke J D. A DNA integrity network in the yeast *Saccharomyces cerevisiae*. Cell 2006; 124(5):1069-81.
54. Huang M E, Kolodner R D. A biological network in *Saccharomyces cerevisiae* prevents the deleterious effects of endogenous oxidative DNA damage. Mol Cell 2005; 17(5):709-20.
55. Scholl C, Frohling S, Dunn I F, Schinzel A C, Barbie D A, Kim S Y, et al. Synthetic lethal interaction between oncogenic KRAS dependency and STK33 suppression in human cancer cells. Cell 2009; 137(5):821-34.

Example III

Material and Methods

Cell Lines

A549, A549δPNKP (A549 stably depleted of PNKP using shRNA), A549-SC (A549 stably expressing a scrambled shRNA), #22 (PTEN$^{-/-}$), #35 (PTEN$^{-/-}$), Neo124 (vector only control of HCT116, PTEN$^{+/+}$), HCT116 (PTEN$^{+/+}$), and all PC3 (naturally PTEN$^{-/-}$) based cell lines were cultured at 37° C. and 5% $CO_2$ in a humidified incubator in a 1:1 mixture of Dulbecco's Modified Eagle's Medium and F12 supplemented with 10% FBS, 50 U/mL penicillin, 50 g/mL streptomycin, 2 mM L-glutamine, 0.1 mM non-essential amino acids and 1 mM sodium pyruvate. All culture supplements were purchased from Invitrogen.

A549 cells were purchased from the American Type Culture Collection (Manassas, Va.). #22, #35, Neo124 and HCT116 parental cell lines were obtained as a gift from the lab of Dr. Robert G. Bristow (University of Toronto). PC3 cells were obtained as a gift from Dr. Alan Ashworth (The Institute of Cancer Research, London, UK).

Materials pSUPER.neo vectors (Oligoengine, Seattle, Wash.) contained either an shRNA directed against nucleotides 1391-1410 of PNKP(1) to stably deplete PNKP in A549 or an shRNA to no known gene target (a scrambled shRNA) to generate the control cell line A549-SC.

The pBABE.puro vectors contained wildtype or mutated PTEN, as well as the one containing wildtype RAD 51, were used to make the PC3 reconstituted cell lines; WT PTEN, p.K289E, p.R55fs*1, WT RAD51, p.BABE.puro and p.C124S.

WT PTEN—full length, wild-type PTEN cDNA
p.K289E—PTEN mutant with reduced nuclear shuttling cDNA
p.R55fs*1—truncation mutant normally found in PC3 cDNA
WT RAD51—full length, wild-type RAD51 cDNA
p.BABE.puro—vector only
p.C124S—phosphatase inactive PTEN mutant cDNA These plasmids were obtained as a gift from Dr. Alan Ashworth (2). The stable transfection protocol is described below. All siRNAs were purchased from Qiagen (Mississauga, ON) with the exception of PNKP, which was purchased from Ambion (Austin, Tex.). A12B4C3 was generated by Dr. Dennis Hall (University of Alberta) and is described previously (3).

Stable Transfections 20,000 cells were plated and allowed to adhere overnight in a 24-well dish at 37° C. and 5% $CO_2$. The transfection mixture was prepared from two separate solutions, the first containing 1 μg of plasmid DNA dissolved in 50 μL, total of Opti-MEM (Invitrogen) and the second 3 μL, of Lipofectamine2000 (Invitrogen) in 50 μL total Opti-MEM. The two solutions were incubated at room temperature for 5 min before combination, mixed and then held at room temperature for 20 min. The media from the pre-plated cells was then removed and the transfection mixture was added and incubated for 24 h at 37° C. and 5% $CO_2$. The cells were then trypsinized and passaged into 6×100-mm plates in DMEM/F12 without antibiotics and incubated overnight at 37° C. and 5% $CO_2$. The following day, media was removed and replaced with complete DMEM/F12 containing 5 μg/mL puromycin for p.BABE.puro constituted cell lines or 500 μg/mL G418 for p.SUPER.neo constituted cell lines. After single-clone of pSUPER.neo constituted colonies were formed (10-18 days) the colonies were picked and expanded prior to protein analysis. pBABE.puro constituted cell lines were used as heterogenous populations and single-clone colonies were not picked.

siRNA Library Screen

Qiagen's "druggable" genome siRNA library was first distributed into 89×96-well plates at a concentration of 1 μM, each well containing four separate siRNAs to the same mRNA target. Also added to the plates were three additional control wells (C12, D12 and E12) of AllStars Negative (ASN) scrambled siRNA (Qiagen). Then, utilizing a JANUS Automated Workstation (PerkinElmer, Waltham, Mass.), 4,000 A549δPNKP or A549(Scramble) cells were seeded into each well of a 96-well plate in a final volume of 100 μL, DMEM/F12 without penicillin/streptomycin and allowed to adhere overnight in a humidified incubator. The following day, transfection mixture was generated as described above (56 nM siRNA and a total of 0.23 μL Dharmafect transfection reagent 1/well), media was aspirated from the plates containing cells, and 100 μL of the mixture was added to each well and allowed to incubate for 72 h. After incubation 10% v/v of 440 μM Alamar Blue (Sigma-Aldrich, Oakville, ON) was added to each well and the cells were incubated for 50-90 min after which the fluorescence in each well was determined using an EnVision 2104 Multilabel Reader (PerkinElmer) with an excitation wavelength of 563 nm and emission wavelength of 587 nm.

Transient Transfection 4,000 cells were plated per well in a 96-well plate, and allowed 24 h to adhere in a humidified incubator at 37° C. and 5% $CO_2$. All wells surrounding samples were filled with 100 μL distilled water to control for evaporation effects. 16 nM final concentration of siRNA was added to 50 μL total reaction volume in Opti-MEM (Invitrogen). At the same time as siRNA-Opti-MEM incubation, a 1:25 dilution of Dharmafect Transfection Reagent 1 (Dharmacon, Lafayette, Colo.) in Opti-MEM was allowed to incubate at room temperature for 5 min, to provide a final volume of 0.12 μL of transfection reagent per well. The two transfection solutions were then combined and held at room temperature for 20 min. The media was then removed from the cells and 100 μL of the transfection mixture was added per well and the plate was incubated at 37° C. and 5% $CO_2$ for 72 h. All siRNAs used here were purchased from Qiagen (Mississauga, ON).

Protein Analysis

Approximately $10^6$ transiently transfected cells were washed twice with ice cold PBS, trypsinized, and spun down at 1500 rpm for 10 min at 4° C. The supernatant was aspirated and the cell pellet was resuspended in 200 μL, of CHAPS buffer (0.5% CHAPS, 137 mM NaCl, 50 mM Tris-HCl pH 7.5, and 1 mM EDTA) and rocked for 1 hour at 4° C., after which cell debris was spun down at 14,000 rpm for 20 minutes at 4° C. Determination of whole cell lysate concentration was then conducted using the Bradford Assay.

Western blots were conducted using 50 μg of whole cell lysate. Monoclonal primary antibodies were incubated 1:1000 in 5% PBSMT overnight at 4° C. (Cell Signaling, Beverly, Mass.). All secondary antibodies were incubated 1:5000 for 45 min at room temperature.

Cell Proliferation Assay

Cell proliferation assays were performed using the transient transfection technique described above, however, after incubation of siRNA for 72 h, 10% v/v of 440 μM Alamar Blue (Sigma-Aldrich, Oakville, ON) was added to each well and the cells were incubated for 50-90 min after which the fluorescence in each well was determined using an EnVision 2104 Multilabel Reader (PerkinElmer) with an excitation wavelength of 563 nm and emission wavelength of 587 nm. HCT116 based cell lines were subjected to a 10.7% v/v 440 μM Alamar Blue solution per well for the same times indicated.

Colony Forming Assay

The effect of survival of simultaneous disruption of two proteins was conducted using the clonogenic survival assay. To allow cells time to adhere to the plates, cells were seeded 24 h in advance. Cells were treated with the PNKP inhibitor A12B4C3 for 9-14 consecutive days in triplicate at 0 μM, 0.1 μM, 1 μM, and 10 μM final concentration where 100 cells were plated for the 0 μM, 0.1 μM and 1 μM concentration groups and 300 cells in the 10 μM concentration group. Colonies were then stained with a crystal violet containing 20% methanol for one hour after which the plates were washed in warm water and left to dry overnight. Colonies of 50+ cells were then counted using an automated colony counter (Oxford Optronix, Oxford, UK).

For the indicated colony-forming assays, cells were treated with 0, 1, 2, 4, 6, or 8 Gy of γ-radiation ($^{60}$Co Gammacell; Atomic Energy of Canada Limited, Ottawa, Canada).

Results—III

We performed a forward transfection using an extensive library of siRNAs targeting 6961 genes using a mixture of four distinct siRNAs targeted each gene. The screen was performed in duplicate using A549 lung cancer cells stably depleted of PNKP (A549δPNKP) and cells expressing a scrambled shRNA (A549-SC) under identical conditions. Cells were exposed to siRNA transfection complexes continuously for 72 h allowing for at least two cell cycles to occur at a concentration known to be effective at knocking down target proteins. Cell survival was then determined by an Alamar Blue-based reduction assay (7).

Figure 22:
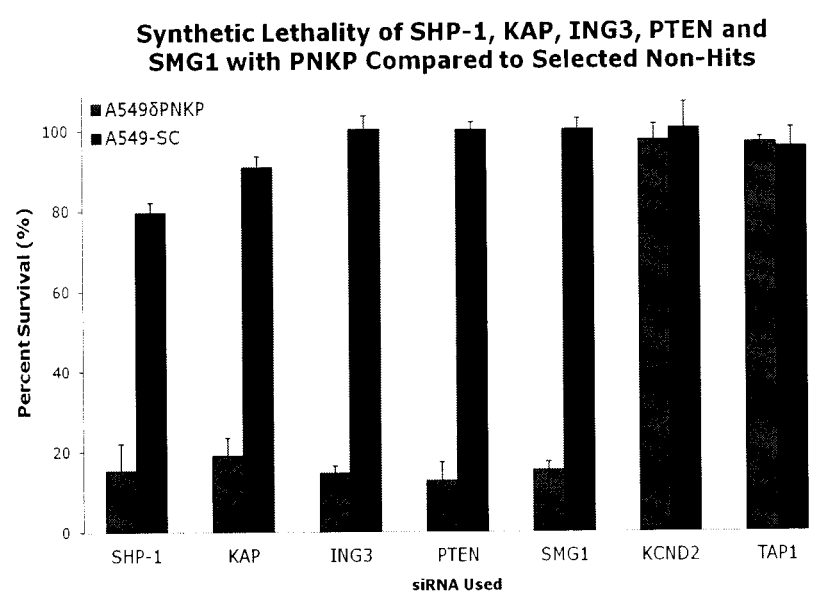
FIG. 22 depicts five selected tumor suppressors identified through screening.
Figure 23:
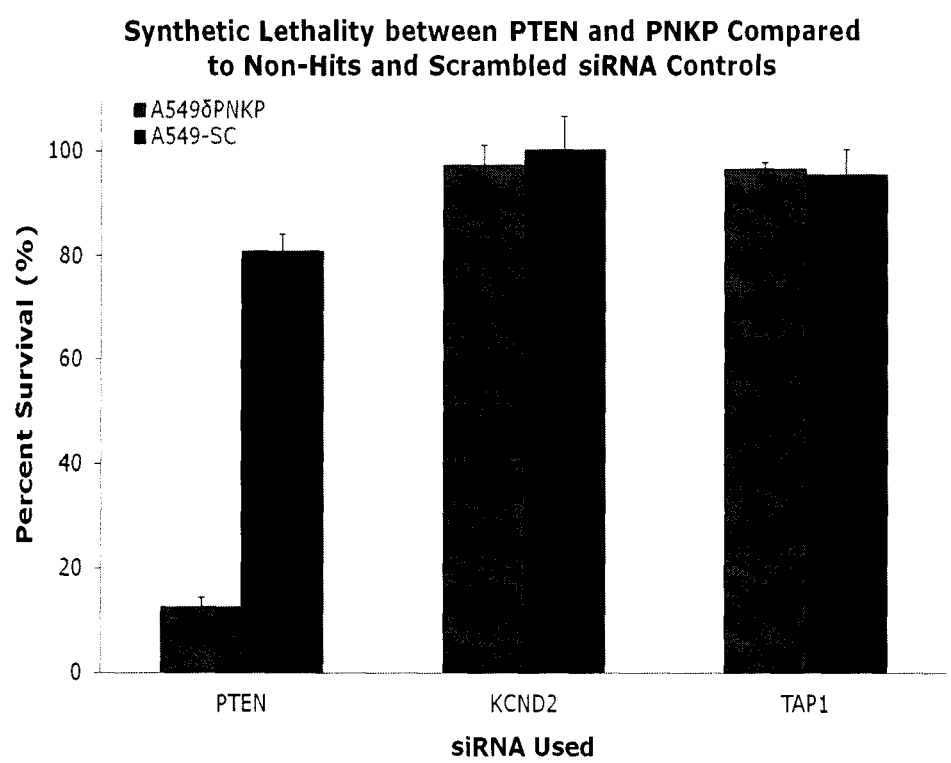
FIG. 23 depicts survival of PTEN-PNKP double disruption compared to two non-hits.

Cell survival scores after targeting each of the 6961 mRNAs were compared to controls located on the same plate. When the duplicate screens were compared to each other, they were shown to be highly reproducible. Amongst the potential synthetic lethal partners of PNKP was the major tumor suppressor PTEN (FIG. 22). This figure shows the difference between five selected tumor suppressors compared to two proteins shown to be not lethal when co-disrupted with PNKP. PTEN is then compared to the same two non-hits (FIG. 23) for emphasis.

Confirmation of PTEN as a Possible Synthetic Lethal Partner of PNKP

PTEN is a potent tumor suppressor located on chromosome 10q23 whose down regulation or complete loss is implicated in the development and/or progression of many types of cancers including; many advance stage sporadic cancers, glioblastomas, prostate, endometrial, brain, skin, breast, and thyroid cancers (8-11). PTEN plays a critical role as an antagonist of the phosphoinositide 3-kinase (PI3K) pathway in the cytoplasm through its lipid phosphatase function by dephosphorylating the 3' position of the second messenger phosphoinositide 3,4,5-triphosphate (PIP3) thereby suppressing downstream signaling events, including those involving PDK1 and Akt/mTOR(8, 12-17). PTEN, in addition to its cytoplasmic roles, also has several important nuclear functions such as: regulation of genomic stability, progression of the cell cycle, cell fate determination and gene expression (16, 18-22).

Figure 24:
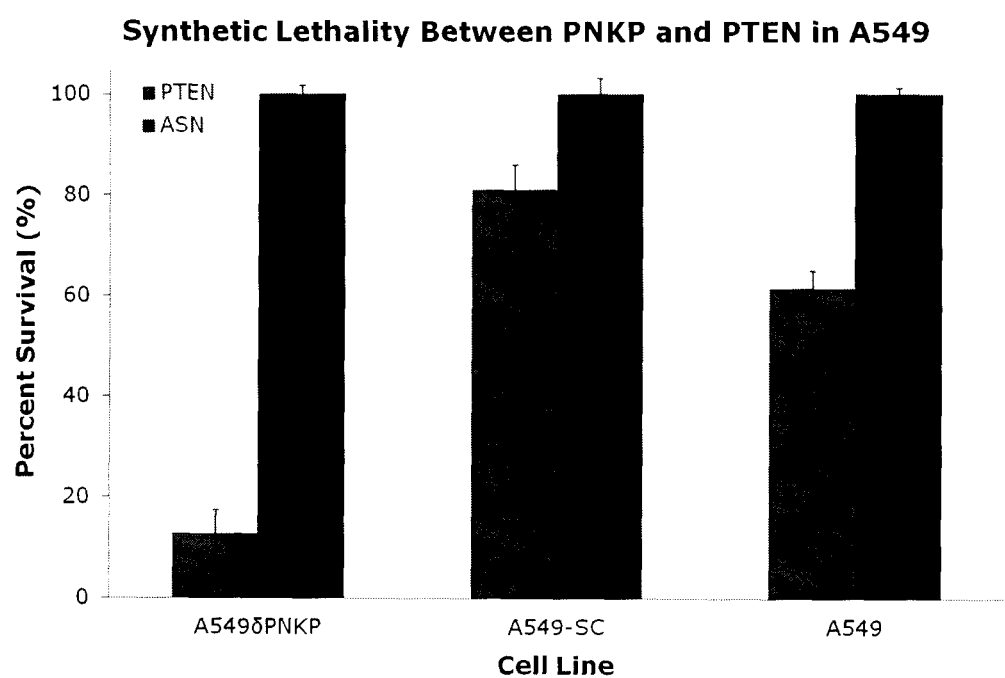
FIG. 24 depicts PTEN-PNKP synthetic lethality.
Figure 25:
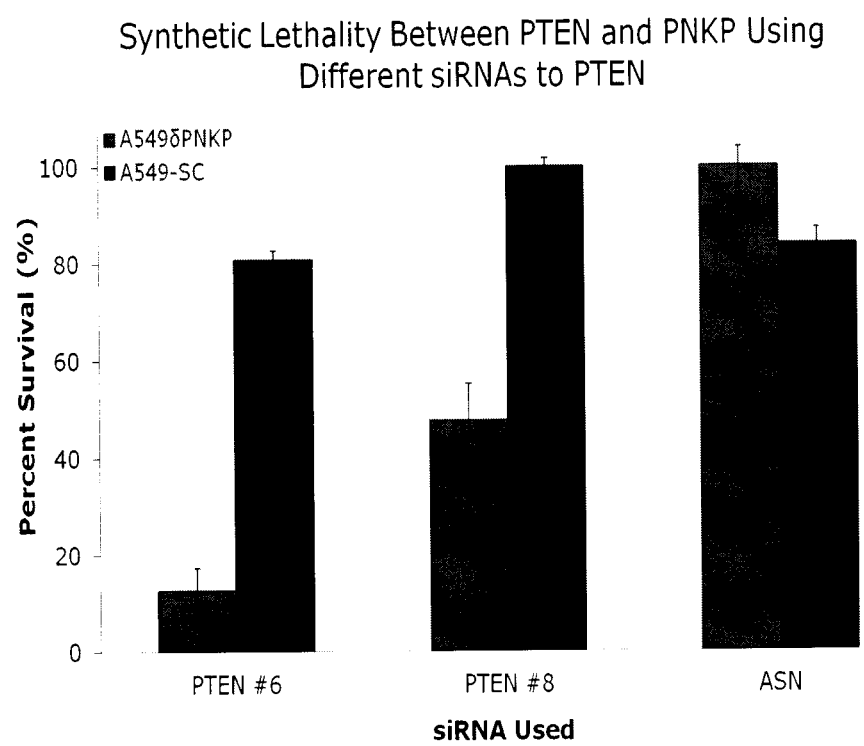
FIG. 25 depicts PTEN-PNKP synthetic lethality.
Figure 26:
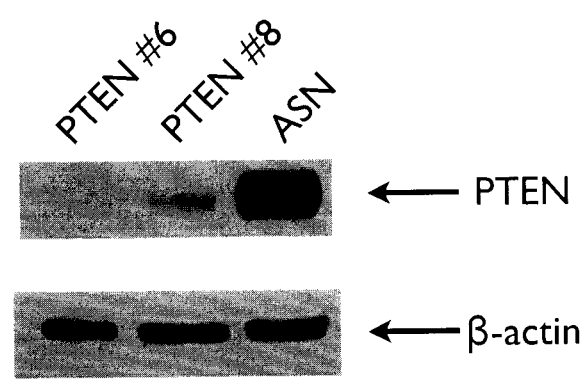
FIG. 26 depicts a Western showing that PTEN levels are different when using different siRNAs.

To confirm the synthetic lethal relationship between PNKP and PTEN, we repeated the analysis, but reduced the concentration of siRNA previously used in the screen by 3.5-fold (FIG. 24) and then used each of the four originally pooled siRNAs separately in order to minimize the potential for off-target effects. When the distinct siRNAs directed against PTEN were assayed, two displayed selective killing of A549δPNKP cells and no toxicity in control cells (FIG. 25, #6 Z-factor=−9.0, p<0.001; #8 Z-factor=−9.1, p<0.001). The survival of the PTEN/PNKP double knock down using PTEN #8 siRNA was higher than when using PTEN #6 siRNA. A western blot using the same conditions as those used in the proliferations assays and suggested that PTEN #8 siRNA is not as effective at knocking down PTEN as PTEN #6 siRNA (FIG. 26). While not wishing to be bound by theory, this level of PTEN may therefore be sufficient to confer additional survival to cells, indicating a potential dose response-like relationship between PTEN and PNKP as it pertains to synthetic lethality.

Figure 27:
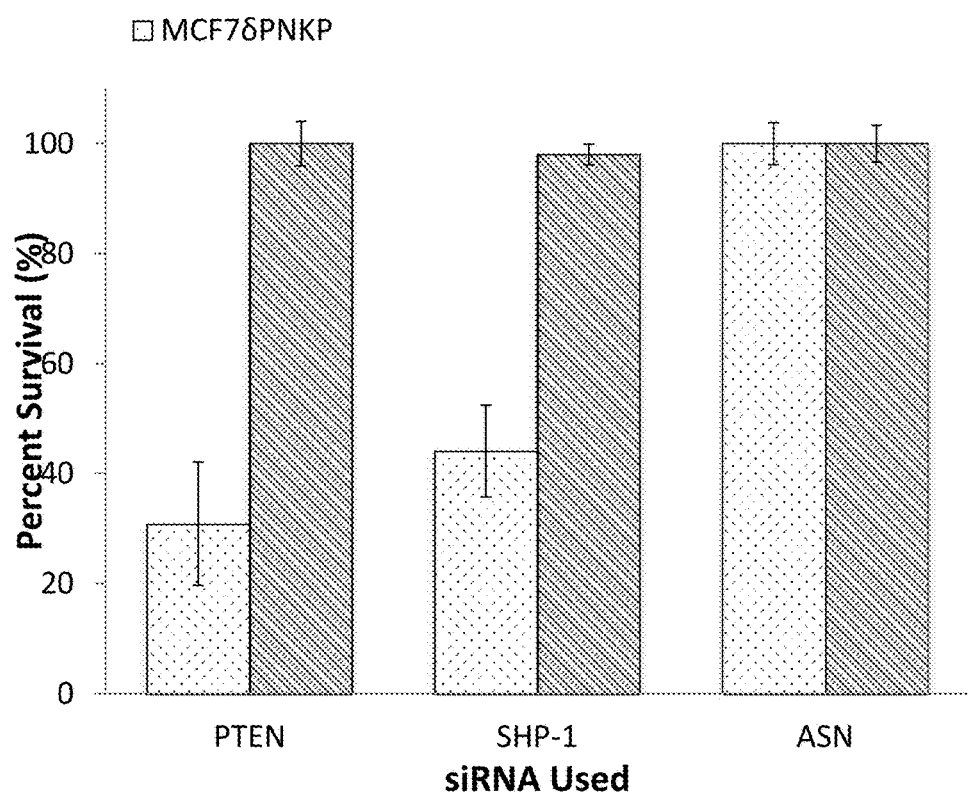
FIG. 27 depicts synthetic lethal partnership in MCF7 cells.

We carried out a similar analysis with the MCF7 breast cancer cell line. We performed the cell proliferation assay using 16 M of PTEN siRNA with an MCF7 cell line stably depleted of PNKP (MCF7δPNKP). The assay was again performed over 72 hours after which Alamar Blue was added at 10% v/v and left for 50-120 minutes. As seen with A549 cells, the combined disruption of both PTEN and PNKP was responsible for lethality, since the depletion of PNKP or PTEN individually was not lethal (FIG. 27, Z-score for PTEN=−8.0, p<0.001, Z-score for SHP-1=−3.4, p<0.001), nor is the activation of RNAi machinery responsible for lethality.

Survival of Isogenically Matched PTEN$^{+/+}$ and PTEN$^{-/-}$ Cells

Figure 28:
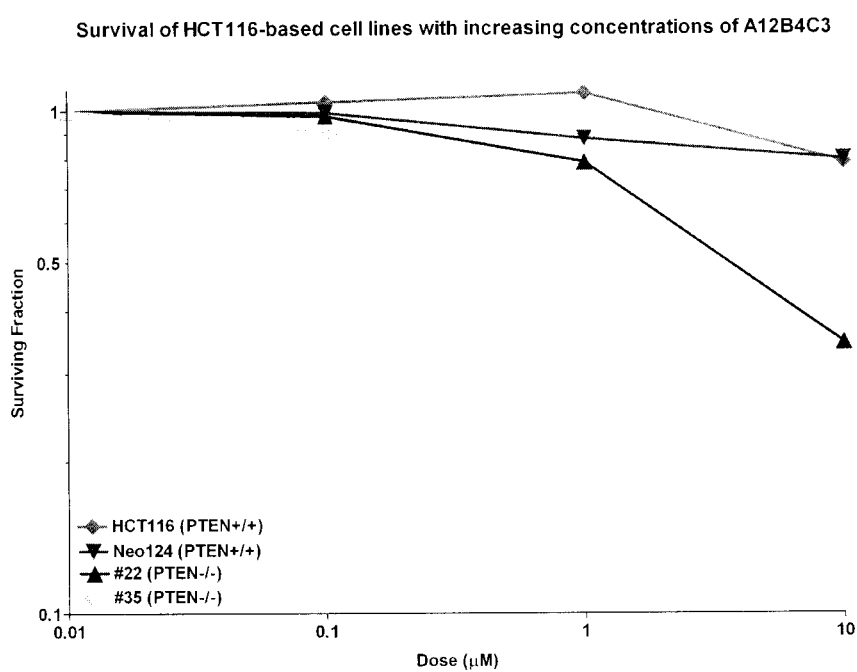
FIG. 28 depicts colony-forming assay testing the survival of isogenically matched HCT116 cells that are PTEN positive or negative under PNKP inhibition.

HCT116 cells isogenically matched PTEN deleted (#22 and #35) and PTEN wildtype cells (HCT116 parental and Neo124 vector only) were subjected to increasing concentrations of the PNKP inhibitor A12B4C3. When PTEN is deleted, cells are sensitive to PNKP disruption, however when those same cells are PTEN proficient, inhibition of PNKP has no effect (FIG. 28). These data indicate PTEN and PNKP are in a synthetic lethal relationship as only when PTEN and PNKP are doubly disrupted do we see a lethal phenotype, singular disruption of PTEN or PNKP alone is not sufficient to confer lethality.

Figure 29A:
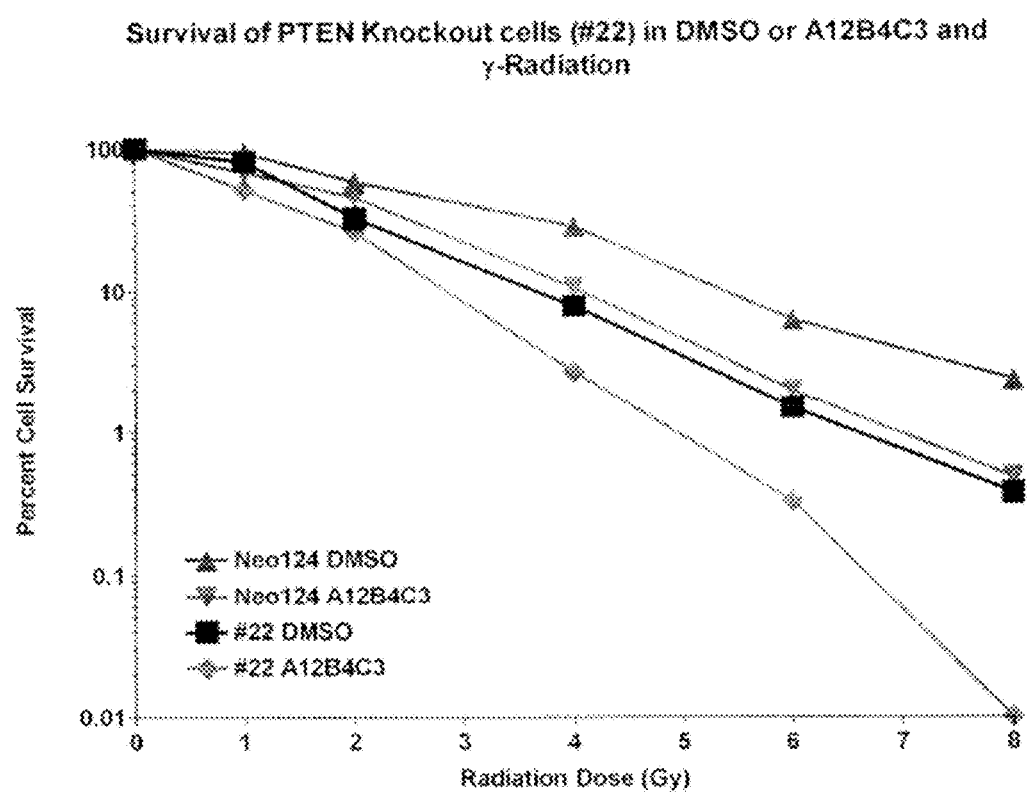
FIGS. 29A and 29B depict utilization of synthetic sickness as a possible therapeutic paradigm.
Figure 29B:
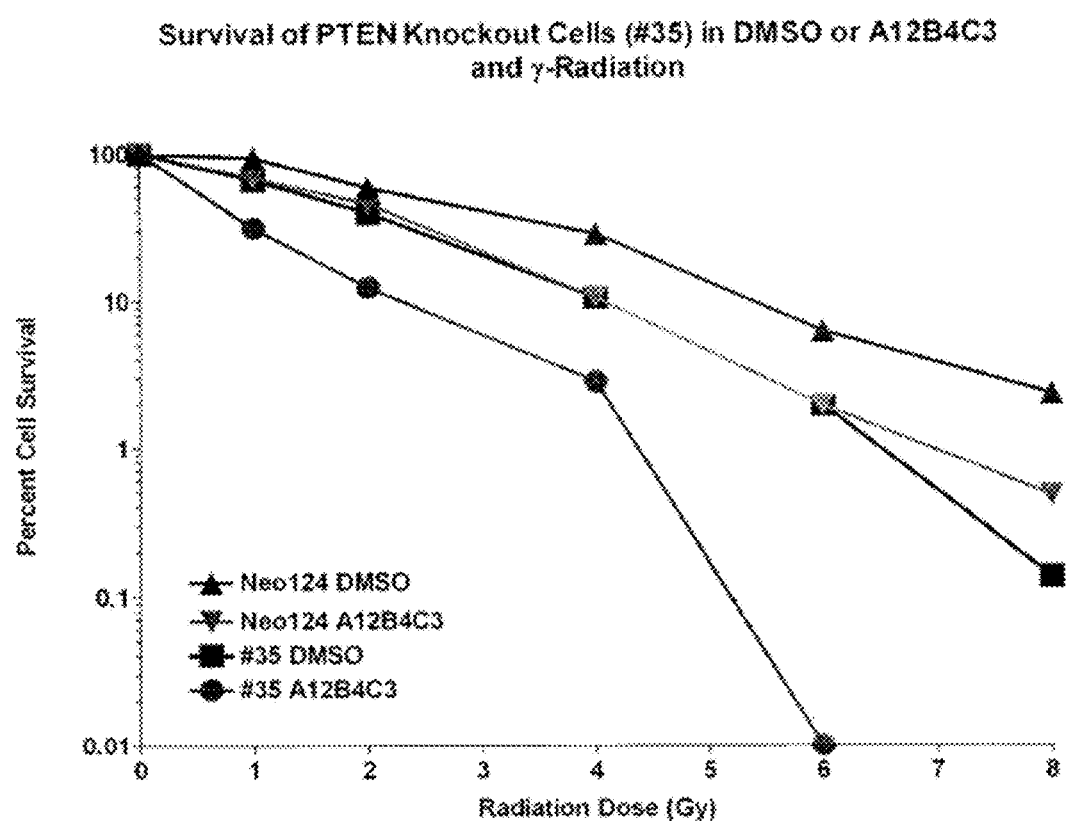
Figure 30:
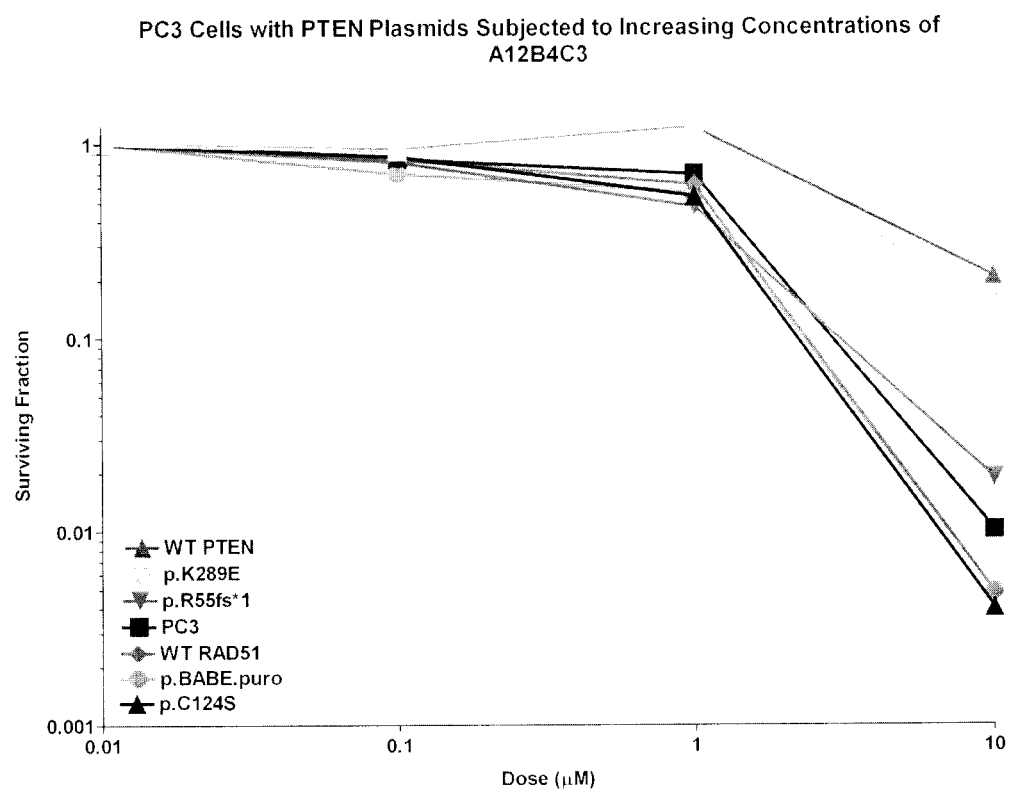
FIG. 30 depicts function of PTEN for lethality, wherein PC3 cells (naturally occurring PTEN negative prostate cancer cells) were transfected with expression vectors encoding various forms of PTEN: WT PTEN—full length, wild-type PTEN cDNA; p.K289E-30 PTEN mutant with reduced nuclear shuttling cDNA; p.R55fs*1—truncation mutant normally found in PC3 cDNA; WT RAD51—full length, wild-type RAD51 cDNA; p.BABE.puro—vector only; p.C124S—phosphatase inactive PTEN mutant cDNA.

These HCT116 cells were then subjected to additional testing to determine if disruption of PNKP in PTEN negative cells would hypersensitize these cells to ionizing radiation. These assays to determine 'synthetic sickness' were done using 2 M A12B4C3, which was added to the cells 24 h before irradiation in a colony-forming assay. After one day the cells were subjected to 0, 1, 2, 4, 6, or 8 Gy of γ-radiation. When either PTEN or PNKP are independently disrupted, there is an increase in sensitivity to ionizing radiation (FIGS. 29 and 30). However, when both PTEN and PNKP are co-disrupted, there is an increase in the sensitivity to ionizing radiation. This demonstrates a therapeutic modality in which PTEN negative tumors are first sensitized using inhibition of PNKP and then targeted using focused radiation. Since PNKP disruption is tolerated well by PTEN proficient cells (i.e., normal cells), there is little damage done to normal tissues and thus side effects should be minimized.

Survival of Naturally Occurring PC3 Negative Cells in Response to PNKP Inhibition To investigate the feasibility of taking advantage of the newly identified partnership between PTEN and PNKP, we subjected the prostate cancer cell line, PC3 (naturally PTEN$^{-/-}$) to an increasing concentration of the PNKP inhibitor A12B4C3 (3) over a period of 12-16 days. The dose response curves (FIG. 30) indicate that at A12B4C3 doses ≥10 μM there was a marked decrease in survival of p.R55fs*1, WT RAD51, p.BABE.puro, p.C124S and PC3 parental cell lines. However, when PC3 cells were reconstituted with either wildtype PTEN or phosphatase proficient but cytoplasmically trapped PTEN (WT PTEN and p.K289E, respectively), lethality under PNKP inhibition was rescued.

REFERENCES

1. Rasouli-Nia A, Karimi-Busheri F, Weinfeld M. Stable down-regulation of human polynucleotide kinase enhances spontaneous mutation frequency and sensitizes cells to genotoxic agents. Proc Natl Acad Sci USA. 2004; 101:6905-10.
2. Mendes-Pereira A M, Martin S A, Brough R, McCarthy A, Taylor J R, Kim J S, et al. Synthetic lethal targeting of PTEN mutant cells with PARP inhibitors. EMBO Mol Med. 2009; 1:315-22.
3. Freschauf G K, Karimi-Busheri F, Ulaczyk-Lesanko A, Mereniuk T R, Ahrens A, Koshy J M, et al. Identification of a small molecule inhibitor of the human DNA repair enzyme polynucleotide kinase/phosphatase. Cancer Res. 2009; 69:7739-46.
4. Bryant H E, Helleday T. Inhibition of poly (ADP-ribose) polymerase activates ATM which is required for subsequent homologous recombination repair. Nucleic Acids Res. 2006; 34:1685-91.
5. Bryant H E, Schultz N, Thomas H D, Parker K M, Flower D, Lopez E, et al. Specific killing of BRCA2-deficient tumours with inhibitors of poly(ADP-ribose) polymerase. Nature. 2005; 434:913-7.
6. Farmer H, McCabe N, Lord C J, Tutt A N, Johnson D A, Richardson T B, et al. Targeting the DNA repair defect in BRCA mutant cells as a therapeutic strategy. Nature. 2005; 434:917-21.
7. Schindler A, Foley E. A functional RNAi screen identifies hexokinase 1 as a modifier of type II apoptosis. Cell Signal. 2010; 22:1330-40.
8. Zhang S, Yu D. PI(3)king apart PTEN's role in cancer. Clin Cancer Res. 2010; 16:4325-30.

9. Li J, Yen C, Liaw D, Podsypanina K, Bose S, Wang S I, et al. PTEN, a putative protein tyrosine phosphatase gene mutated in human brain, breast, and prostate cancer. Science. 1997; 275:1943-7.
10. Ali I U, Schriml L M, Dean M. Mutational spectra of PTEN/MMAC1 gene: a tumor suppressor with lipid phosphatase activity. J Natl Cancer Inst. 1999; 91:1922-32.
11. Liaw D, Marsh D J, Li J, Dahia P L, Wang S I, Zheng Z, et al. Germline mutations of the PTEN gene in Cowden disease, an inherited breast and thyroid cancer syndrome. Nat Genet. 1997; 16:64-7.
12. Myers M P, Stolarov J P, Eng C, Li J, Wang S I, Wigler M H, et al. P-TEN, the tumor suppressor from human chromosome 10q23, is a dual-specificity phosphatase. Proc Natl Acad Sci USA. 1997; 94:9052-7.
13. Tamura M, Gu J, Matsumoto K, Aota S, Parsons R, Yamada K M. Inhibition of cell migration, spreading, and focal adhesions by tumor suppressor PTEN. Science. 1998; 280:1614-7.
14. Mounir Z, Krishnamoorthy J L, Robertson G P, Scheuner D, Kaufman R J, Georgescu M M, et al. Tumor suppression by PTEN requires the activation of the PKR-eIF2alpha phosphorylation pathway. Sci Signal. 2009; 2:ra85.
15. Raftopoulou M, Etienne-Manneville S, Self A, Nicholls S, Hall A. Regulation of cell migration by the C2 domain of the tumor suppressor PTEN. Science. 2004; 303:1179-81.
16. Carracedo A, Alimonti A, Pandolfi P P. PTEN level in tumor suppression: how much is too little? Cancer Res. 2011; 71:629-33.
17. Wong K K, Engelman J A, Cantley L C. Targeting the PI3K signaling pathway in cancer. Curr Opin Genet Dev. 2010; 20:87-90.
18. Salmena L, Carracedo A, Pandolfi P P. Tenets of PTEN tumor suppression. Cell. 2008; 133:403-14.
19. Semba S, Satake S, Matsushita M, Yokozaki H. Phosphatase activity of nuclear PTEN is required for CDX2-mediated intestinal differentiation of gastric carcinoma. Cancer Lett. 2009; 274:143-50.
20. Rankin S L, Guy C S, Mearow K M. PTEN downregulates p75NTR expression by decreasing DNA-binding activity of Sp1. Biochem Biophys Res Commun. 2009; 379:721-5.
21. Jacob A I, Romigh T, Waite K A, Eng C. Nuclear PTEN levels and G2 progression in melanoma cells. Melanoma Res. 2009; 19:203-10.
22. Mosessian S, Avliyakulov N K, Mulholland D J, Boontheung P, Loo J A, Wu H. Analysis of PTEN complex assembly and identification of heterogeneous nuclear ribonucleoprotein C as a component of the PTEN-associated complex. J Biol Chem. 2009; 284:30159-66.

Example—IV

Experiments we undertaken in which new compounds were assayed for their ability inhibit hPNKP phosphatase activity.

Figure 31:
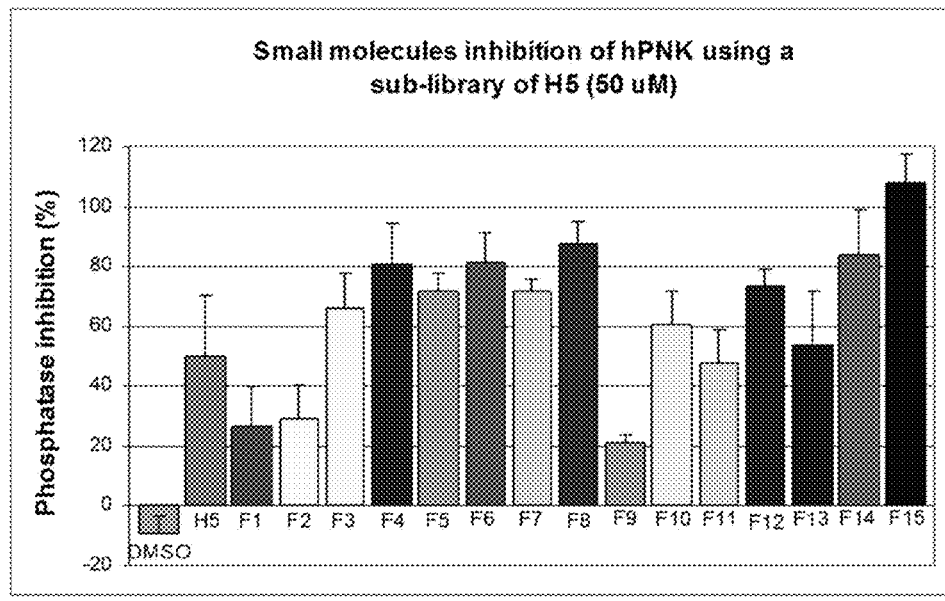
FIG. 31 is a bar graph depicting small molecule inhibition of hPNK using a sub-library of H5 (50 μM)
Figure 32:
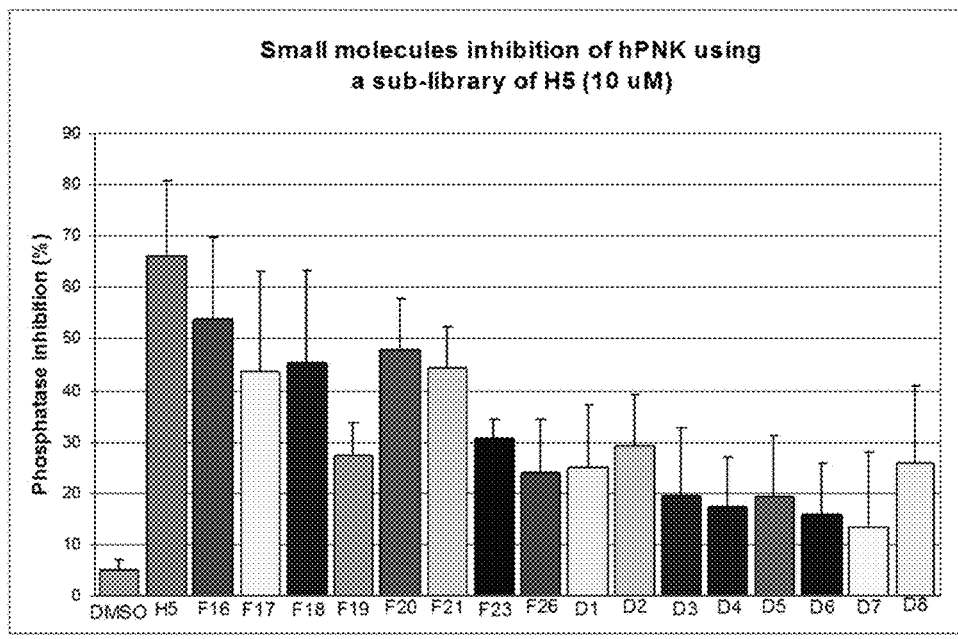
FIG. 32 is a bar graph depicting small molecule inhibition of hPNK using a sub-library of H5 (10 μM)

FIG. 31 is a bar graph depicting small molecule inhibition of hPNK using a sub-library of H5 (50 μM);

FIG. 32 is a bar graph depicting small molecule inhibition of hPNK using a sub-library of H5 (10 μM); and FIG. 33 depicts chemical structure and name of inhibitors of PKNP.

All publications, patents and patent applications mentioned in this Specification are indicative of the level of skill of those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

We claim:

1. A method for the treatment of a subject having lung cancer, or suspected of having lung cancer, said lung cancer associated with a defect in a tumour suppressor, wherein said tumour suppressor is ING3, CDKN3, PTPN6, PTEN, or SMG1, comprising: administering to said subject an inhibitor of PNKP, wherein said subject is human, wherein said inhibitor of PNKP is a RNA interference molecule.

2. The method of claim 1, wherein said RNA interference molecule is a RNAi molecule, a siRNA molecule, or a shRNA molecule.

3. The method of claim 1, further comprising administering a small molecule inhibitor of PNKP.

4. The method of claim 3, wherein said small molecule inhibitor of PNKP comprises: 2-(1-hydroxyundecyl)-1-(4-nitrophenylamino)-6-phenyl-6,7a-dihydro-1H-pyrrolo [3,4-b] pyridine-5,7(2H,4aH)-dione (A12B4C3); 2-(hydroxy(phenyl)methyl)-1-(4-nitrophenylamino)-6-phenyl-6,7a-dihydro-1H-pyrrolo [3,4-b]pyridine-5,7(2H,4aH)-dione (A1B4C3); 2-(hydroxy(3,4,5-trimethoxyphenyl)methyl)-1-(4-nitrophenylamino)-6-phenyl-6,7a-dihydro-1H-pyrrolo[3,4-b]pyridine-5,7(2H,4aH)-dione (A6B4C3); tert-butyl 2-(1-hydroxy-2,2-diphenylethyl)-6-methyl-5,7-dioxo-2,4a,5,6,7,7a-hexahydro-1H-pyrrolo [3,4-b] pyridin-1-ylcarbamate (A26B11C2); 2-(hydroxy(thiophen-2-yl)methyl)-6-methyl-1-(phenylamino)-6,7a-dihydro-1H-pyrrolo [3,4-b]pyridine-5,7(2H,4aH)-dione (A39B1C2); (2R,4aR,7aS)-2-[(1R)-(1-hydroxyundecanyl)]-6-phenyl-1-[(4-nitrophenyl)amino]-4a,7a-dihydro-1H-pyrrolo [3,4-b]pyridine-5,7(2H,6H)-dione (H5); (2R,4 aR,7aS)-2-[(1R)-1-hydroxypropyl]-6-phenyl-1-[(4-nitrophenyl)amino]-4a,7a-dihydro-1H-pyrrolo [3,4-b] pyridine-5,7(2H,6H)-dione(D5); {4-[(2R,4aR,7aS)-2-[(1R)-1-hydroxyundecanyl]-1-[(4-nitrophenyl)amino]-5,7-dioxo-1,2,4a,5,7,7a-hexahydro-6H-pyrrolo[3,4-b]pyridin-6-yl] phenyl} methanaminium chloride (F15); (2R,4aR,7aS)-2-(1-hydroxymethyl)-6-phenyl-1-[(4-nitrophenyl)amino]-4a, 7a-dihydro-1H-pyrrolo [3,4-b]pyridine-5,7(2H,6H)-dione (D7); or (2R,4aR,7aS)-2-[(1R)-(1-hydroxyundecanyl)]-6-(3,4,5-trimethoxyphenyl)-1-[(4-nitrophenyl)amino]-4a,7a-dihydro-1H-pyrrolo [3,4-b]pyridine-5,7 (2H,6H)-dione (F8).

5. A method for the treatment of a subject having breast, or suspected of having breast cancer, said breast cancer associated with a defect in a tumour suppressor, wherein said tumour suppressor is ING3, CDKN3, PTEN, or SMG1, comprising: administering to said subject an inhibitor PNKP, wherein said subject is human, wherein said inhibitor of PNKP is a RNA interference molecule.

6. The method of claim 5, wherein said RNA interference molecule is a RNAi molecule, a siRNA molecule, or a shRNA molecule.

7. The method of claim 6, further comprising administering a small molecule inhibitor of PNKP.

8. The method of claim 5, further comprising administering a small molecule inhibitor of PNKP.

9. The method of claim 8, wherein said small molecule inhibitor of PNKP comprises: 2-(1-hydroxyundecyl)-1-(4-nitrophenylamino)-6-phenyl-6,7a-dihydro-1H-pyrrolo [3,4-b] pyridine-5,7(2H,4aH)-dione (A12B4C3); 2-(hydroxy (phenyl)methyl)-1-(4-nitrophenylamino)-6-phenyl-6,7a-dihydro-1H-pyrrolo[3,4-b]pyridine-5,7(2H,4aH)-dione (A1B4C3); 2-(hydroxy(3,4,5-trimethoxyphenyl)methyl)-1-(4-nitrophenylamino)-6-phenyl-6,7a-dihydro-1H-pyrrolo[3, 4-b]pyridine-5,7(2H,4aH)-dione (A6B4C3); tert-butyl 2-(1-hydroxy-2,2-diphenylethyl)-6-methyl-5,7-dioxo-2,4a,5,6,7, 7a-hexahydro-1H-pyrrolo [3,4b] pyridin-1-ylcarbamate (A26B11C2); 2-(hydroxy(thiophen-2-yl)methyl)-6-methyl-1-(phenylamino)-6,7adihydro-1H-pyrrolo [3,4-b]pyridine-5,7(2H,4aH)-dione (A39B1C2); (2R,4aR,7aS)-2-[(1R)-(1-hydroxyundecanyl)]-6-phenyl-1-[(4-nitrophenyl)amino]-4a, 7adihydro-1H-pyrrolo [3,4-b]pyridine-5,7(2H,6H)-dione (H5); (2R,4 aR,7aS)-2-[(1R)-1-hydroxypropyl]-6-phenyl-1-

[(4-nitrophenyl)amino]-4a,7a-dihydro-1H-pyrrolo [3,4-b]pyridine-5,7(2H,6H)-dione(D5); {4-[(2R,4aR,7aS)-2-[(1R)-1-hydroxyundecanyl]-1-[(4-nitrophenyl)amino]-5,7-dioxo-1,2,4a,5,7,7a-hexahydro-6H-pyrrolo[3,4-b]pyridin-6-yl] phenyl} methanaminium chloride (F15); (2R,4aR,7aS)-2-(1-hydroxymethyl)-6-phenyl-1-[(4-nitrophenyl)amino]-4a,7a-dihydro-1H-pyrrolo [3,4-b]pyridine-5,7(2H,6H)-dione (D7); or (2R,4aR,7aS)-2-[(1R)-(1-hydroxyundecanyl)]-6-(3,4,5-trimethoxyphenyl)-1-[(4-nitrophenyl)amino]-4a,7a-dihydro-1H-pyrrolo [3,4-b]pyridine-5,7 (2H,6H)-dione (F8).

\* \* \* \* \*